US005972982A

United States Patent [19]
Nair et al.

[11] Patent Number: 5,972,982
[45] Date of Patent: Oct. 26, 1999

[54] HETEROARYL-SUBSTITUTED DEOXY GLYCEROLS AND ANTIBACTERIAL AND ANTIVIRAL COMPOSITIONS CONTAINING THE SAME

[75] Inventors: Haridasan K. Nair, Williamsville, N.Y.; Andrew C. Peterson, Madison, Wis.; Friedrich Paltauf; Albin Hermetter, both of Graz, Austria; Rudolf Franzmair, Linz, Austria

[73] Assignee: Clarion Pharmaceuticals Inc., Madison, Wis.

[21] Appl. No.: 08/946,529

[22] Filed: Oct. 7, 1997

Related U.S. Application Data

[63] Continuation-in-part of application No. 08/485,427, Jun. 7, 1995, Pat. No. 5,707,978, which is a continuation-in-part of application No. 08/344,282, Nov. 22, 1994, abandoned.

[51] Int. Cl.$^6$ .......... A61K 31/41; A61K 31/415; C07D 249/08; C07D 233/56
[52] U.S. Cl. .......... 514/383; 514/399; 514/406; 514/415; 548/255; 548/267.8; 548/257; 548/260; 548/262.4; 548/341.1; 548/376.1; 548/509
[58] Field of Search .......... 548/341.1, 255, 548/267.8, 257, 260, 262.4, 376.1, 509; 514/399, 383, 406, 415; 424/400, 450

[56] References Cited

U.S. PATENT DOCUMENTS 4,036,974  7/1977  Walker et al. .......... 424/273
5,116,992  5/1992  Braquet et al. .......... 514/77

FOREIGN PATENT DOCUMENTS 0148777  7/1985  European Pat. Off. .
0157609A2  10/1985  European Pat. Off. .

OTHER PUBLICATIONS

DeClerq et al., (S)–9–2,3–Dihydroxypropyl)adenine: An aliphatic Nucleoside Analog with Broad–Spectrum Antiviral Activity, *Science* (1978), 200: 563–565.

DeClerq et al., A novel selective broad–spectrum anti–DNA virus agent, *Nature* (1986), 323: 464–467.

Ueda et al., Synthesis of N–(2,3–Dihydroxypropyl) Derivatives of Nucleic Bases, *J. Heterocyl. Chem.* (1971), 8: 827–829.

Hiller et al., Abstract, *Nucleic Acids Research* (1976), 3: 721–727.

Holy et al., Synthesis of New Mono– and disubstituted hydroxyalkyl and Aminoalkyl Derivatives of Heterocyclic Bases, *Collect. Czech. Chem. Comm.* (1978), 43: 3444–3465.

Holy et al., Acyclic Nucleotide Analogs Derived from 8–Asapurines: Synthesis and Antiviral Activity, *J. Med. Chem.* (1996), 39: 4073–4088.

Bittman et al., Isosteric Phosphonate Analogs of ET–16–OMe. Synthesis and Biological Evaluation of the Enantimoers of 2'–(Trimethylammonio)ethyl–(Hexacecyloxy)–3–methoxybutanephosphonate and 2'–(Trimethylammonio)ethyl–4–(Hexadecylthio–3–methoxybutanephosphonate, *J. Med. Chem.* (1994), 37: 425–430.

W. Rospond and J. Chlebicki, Synthesis of Higher 1–(Methyl and Dimethyl)amino–3–Alkylthio–2–Propanols and 1–(Ethyl or Diethyl)Amino–3–Alkylthio–2–Propanols, *Polish J. Chem.* (1984), 58: 593–597.

Rosenberg et al., Phosphonylmethoxyalkyl and Phosphonylalkyl Derivatives of Adenine, *Collect. Czech. Chem. Commun.* (1988) 53: 2753–2777.

V.J. Klosa, Über die Umsetzung von Chinasolon–(4)–derivaten mit Alkylenoxiden, *J. Prakt. Chem.* (1966), 4: 34–40.

Mislyuk et al., Kinetics of the Reaction of Piperazine with 1–R–2,3–Epoxypropanes, *J. Org. Chem. USSR* (*Engl. Transl*) (1986), 22(12): 2247–2252.

A. Hermetter and F. Paltauf, Procedures for Synthesis of Ether Lipids, pp. 391–393 et seq., H.K. Mangold and F. Paltauf, Ether Lipids, Academic Press, (1983).

(List continued on next page.)

Primary Examiner—Joseph K. McKane
Attorney, Agent, or Firm—DeWitt Ross & Stevens S.C.; Salvatore R. Conte, Esq.

[57]  ABSTRACT

Heteroaryl-substituted deoxy glycerols represented by the general Formulas Ia, Ib and Ic:

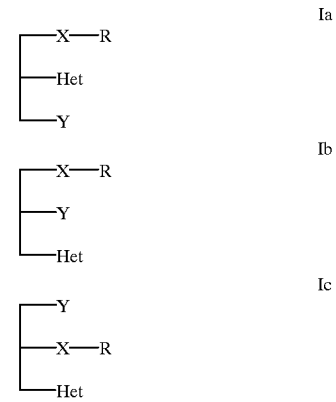

wherein: X is oxygen (—O—) or sulfur (—S—); R is substituted or unsubstituted straight or branched chain $C_{1-30}$ alkyl or alkenyl, provided that a double bond of the alkenyl does not originate at the carbon atom bound to the X substituent; Het is a 5- to 9-membered heteroaryl mono- or bicyclic ring system having no more than 1 carbonyl carbon in the ring system, with 1 to 4 nitrogen atoms as the sole heteroatoms, one of which nitrogens is bonded to the glycero carbon; and Y is hydroxyl (—OH) or thiol (—SH), pharmaceutical compositions containing the same, and methods of using the compounds, are disclosed. The compounds exhibit antiviral and antibacterial activities.

33 Claims, No Drawings

OTHER PUBLICATIONS

F. Paltauf and A. Hermetter, Preparation of Alkyl Ether and Vinyl Ether Substrates for Phospholipases, *Methods Enzym.* (1991) 197: 134–149.

A. Hermetter and F. Paltauf, A New Method for the Detritylation of 1,2–Diradyl–3–O–Tritylglycerols, *Chem. Phys. Lipids* (1981), 29: 191.

S. Zalipsky et al., A convenient general method for synthesis of $N^\alpha$–or $N^\omega$–dithiasuccinoyl (Dts) amino acids and dipeptides: application of polyethylene glycol as a carrier for functional purification, *Int. J. Peptide Protein Res.* (1987), 30: 740–783.

P.N. Guivisdalsky and Bittman, Glycidyl Derivatives as Chiral $C_3$ Synthons. Ring Opening Catalyzed by $BF_3$ Etherate, *J. Am. Chem. Soc.* (1989), 111: 3077–3079.

B. Cimetiere and J.M. Julia, Optically active oxiranes Synthesis of PAF (Platelet Aggregating Factor), *Bull. Soc. Chim. Fr.* (1991) 128:926–938.

Rattay et al., Influence of $\alpha$–branched fatty acid chains on the thermotropic behaviour of racemic 1–O–hexadecyl–2–acyl–glycero–3–phosphocholines, *Chem. Phys. Lipids* (1995), 75: 81–91.

T.K. Todsen et al., Some $\beta$–Hydroxypropyl Sulfides and their Derivatives, *J. Am. Chem. Soc.* (1950), 72: 4000–4002.

W. Rospond and J. Chlebicki, Reactions of 1–Alkythio–2, 3–Epoxypropanes With Ethanolamines, *Polish J. Chem.* (1984), 58: 1237–1242.

E.O. Oswald et al., The Synthesis of $^{14}C$– and $^{3}H$–Labeled Glycerol Ethers, *Lipids* (1966), 1: 121.

HETEROARYL-SUBSTITUTED DEOXY GLYCEROLS AND ANTIBACTERIAL AND ANTIVIRAL COMPOSITIONS CONTAINING THE SAME

This is a Continuation-in-Part of application Ser. No. 08/485,427, filed 7 Jun. 1995 now U.S. Pat. No. 5,707,778, which is a Continuation-In-Part of application Ser. No. 08/344,282, filed 22 Nov. 1994 and now abandoned.

FIELD OF THE INVENTION

The invention is directed to deoxy glycerols substituted with a heteroaromatic cyclic moiety on the glyceryl backbone and to antibacterial and antiviral pharmaceutical compositions containing the same. The compounds possess antiviral and antibacterial activities.

DESCRIPTION OF THE PRIOR ART

Glycerols substituted by an aryl heterocycle, such as purine, adenine and the like, have been shown to exhibit antiviral activity. For example, the broad spectrum antiviral activity of (S)-9-(2',3'-dihydroxypropyl)adenineand (S)-9-(3'-dihydroxy-2'-phosphonylmethoxypropyl)adenine against several DNA and RNA viruses is reported in DeClercq et al., Science (1978) 200: 563–565 and DeClercq et al., Nature (1986) 323: 464–467. Glycerol derivatives in which one hydroxy group is substituted by a heterocycle, such as, adenine, cytosine, uracil, and the like, are reported in the literature. See, for example, Ueda et al., J. Heterocyl. Chem. (1971) 8: 827–829; Hiller et al., Nucleic Acids Research (1976) 3: 721–727; A. Holy et al., Collect. Czech. Chem. Commun., (1978) 43: 3444–3465; and A. Holy et al., J. Med. Chem., (1996) 39: 4073–4088.

The synthesis of glycerol derivatives in which one hydroxy is substituted by a heterocycle has been reported. The synthesis of 9-(S)-(2,3-dihydroxypropyl)-8-azaadenine and 8-(S)-(2,3-dihydroxypropyl-8-azaadenine is described in A. Holy et al., J. Med. Chem., (1996) 39: 4073–4088. The synthesis of 1-(alkyl)- and 1-(dialkyl)-amino-3-alkylthio-3-propanols where alkyl is methyl or ethyl is described by W. Rospond and J. Chlebicki, Polish J. Chem., (1984) 58:593–597.

The preparation of 1-O-alkylglycerol derivatives in which one of the hydroxyl groups has been substituted by a nucleotide base has been described. The preparation of (RS)-(2-hydroxy-3-octyloxypropyl)-9-adenine, also referred to as 2-(adenin-9-yl)propane-1,3-diol, is reported by Rosenberg et al., Collect. Czech. Chem. Commun. (1988) 53:2753–2777; the synthesis of (RS)-3-(2-hydroxy-3-dodecyloxypropyl)quinazalin-4-one is described by V. J. Klosa, J. Prakt. Chem. (1966) 4: 34–40. Also reported is the synthesis of (RS)-1-(2'-hydroxy-3'-butyloxypropyl) piperazine by Mislyuk et al., J. Org. Chem USSR (Engl. Transl.), (1986) 22(12): 2247–2252.

The synthesis of 1-O-alkylglycerols in which one of the hydroxyl groups has been substituted by an amine has been reported. Glycerols bearing a non-cyclic $NR^1R^2$ substituent in the 2-position and a lower $C_{1-5}$ alkyl ether substituent in the 1-position are disclosed in U.S. Pat. No. 5,116,992. 1-O-Alkylglycerols bearing a cyclic, aliphatic amine substituent in the 2-position have been reported in EPO Application No. 0157609A2. A method for producing 1-O-Alkylglycerols featuring a cyclic imide moiety, such as phthalimido, substituent in the 2-position and a 1-O-alkyl group of 10 to 21 carbons was described in EPO 0148777. 1-{2-(Alkyl-thio(oxy))-3-(alkyl-thio(oxy)) propyl}imidazoles are described in U.S. Pat. No. 4,036,974.

These ethers are noted as having antimicrobial utility. This patent also describes the synthesis of intermediate 1-(3-alkoxy-2-hydroxypropyl)imidazoles wherein the carbon skeleton of the alkyl group contains twelve or fewer carbons. No pharmacological activity is described for the intermediates.

Applicants are unaware, however, of any prior art which describes the heteroaryl-substituted fatty alkyl and alkenyl ether glycerols disclosed and claimed herein.

DETAILED DESCRIPTION OF THE INVENTION

The invention is drawn to novel, therapeutically active heteroaryl-substituted deoxy glycerols represented by the general Formulas Ia, Ib and Ic (collectively referred to herein as "Formula I compounds"):

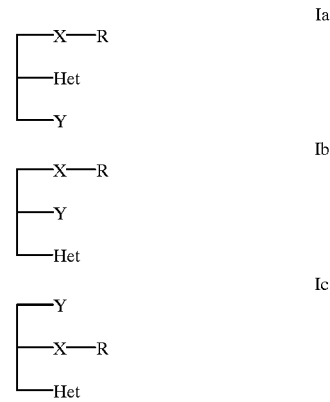

wherein:
  X is oxygen (—O—) or sulfur (—S—);
  R is selected from the group consisting of substituted or unsubstituted straight or branched chain $C_1$–$C_{30}$ alkyl or alkenyl, provided that a double bond of the alkenyl does not originate at the carbon atom bound to the X substituent, R being optionally substituted with one or more of halo, $C_1$–$C_3$ alkoxy, or cyano;
  Het represents a 5- to 9-membered heteroaryl mono- or bicyclic ring system having no more than 1 carbonyl carbon in the ring system, with 1 to 4 nitrogen atoms as the sole heteroatoms, one of which nitrogens is bonded to the glycero carbon;
  Y is hydroxyl (—OH) or thiol (—SH); and
  all enantomeric and cis- and trans-geometric isomers thereof and all pharmaceutically-suitable salts thereof.

When the R substituent is an alkyl, it is preferred that R is a $C_{14-20}$ alkyl, and it is most preferred that R is a $C_{16-18}$ alkyl. When the R substituent is an alkenyl, it is preferred that R is a $C_{14-20}$ alkenyl, and it is most preferred that R is a $C_{16-18}$ alkenyl.

The R substituent may be optionally substituted one or more times, preferably once, with substituents which do not interfere with the synthesis of the compounds. Preferably, substituents on the R group are selected from halo, $C_{1-3}$ alkoxy, or cyano. The term "halo" denotes chloro, bromo, iodo and fluoro, with chloro and fluoro being preferred.

Typical of the heteroaryl ring moieties included within the term "Het" are 5- to 9- membered rings, including single and fused rings having no more than 1 carbonyl carbon in the ring system such as pyrrolyl, pyrazolyl, imidazolyl, 1,2,3-triazolyl, 1,2,4-triazolyl (also denoted as 1-triazolyl), tetrazol-1-yl, indolyl, benzimidazolyl, benztriazolyl, and the like, with imidazolyl and triazolyl being preferred. The Het substituent may also be optionally substituted with one or more substituents, including $C_{1-3}$ alkyl, $C_{1-3}$ alkoxy or a polar substituent such as cyano, nitro, or methylsulfono. Typical of such substituted heteroaryl ring moieties are, for example, 1-(2-methylimidazolyl), 1-(4-methoxyindolyl), 1-(4-cyano-benztriazolyl), and the like. As used hereinafter, the term "Het-compound" represents the heteroaryl ring moiety with its additional hydrogen (i.e., "Het-H"), for example, pyrrole, pyrazole, imidazole, triazole, etc.

The most preferred Formula 1 compounds are those wherein R is $C_{16-18}$, alkyl and Het is imidazolyl or triazolyl, for example:

1-O-octadecyl-2-(1-imidazolyl)-2-deoxy-glycerol, also known as CPR1005 herein;

1-O-octadecyl-2-(1-triazolyl)-2-deoxy-glycerol, also known as CPR 1004 herein; and 1-O-hexadecyl-2-(1-imidazolyl)-2-deoxy-glycerol, also known as CPR 1104 herein.

The preferred compounds of Formula Ia are:

1-O-hexadecyl-2-(1-(4-methoxyindolyl))-2-deoxy-glycerol;

1-O-tetraeicosyl-2-(1-tetrazolyl)-2-deoxy-glycerol

1-O-hexadecyl-2-(1-(4-cyanobenztriazolyl))-2-deoxy-glycerol;

1-O-(trans-9-octadecenyl)-2-(1-imidazolyl)-2-deoxy-glycerol; and

The preferred compounds of Formula Ib are:

1-O-octadecyl-3-(1-imidazolyl)-3-deoxy-glycerol,also known as CPR 1150;

R-1-O-hexadecyl-3-(1-imidazolyl)-3-deoxy-glycerol;

1-O-octadecyl-3-(1-indolyl)-3-deoxy-glycerol;

1-O-(cis-8-hexadecenyl)-3-(1-tetrazolyl)-3-deoxy-glycerol; and

1-O-hexadecyl-3-(1–2 '-methylimidazolyl)-3-deoxy-glycerol.

The preferred compounds of Formula Ic are:

1-(1-imidazolyl)-1-deoxy-2-O-hexadecyl-glycerol;

1-(1-triazolyl)-1-deoxy-2-O-(2-chloro-octadecyl)-glycerol;

1-pyrrolyl-1-deoxy-2-O-(2-methoxy-octadecyl)-glycerol; and 1-(1-tetrazolyl)- 1-deoxy-2-O-(9-octadecenyl)-glycerol.

CHEMISTRY

All of the references cited herein below are incorporated by reference in their entireties The Formula I compounds are prepared by the stepwise procedures outlined in the following Reaction Schemes and subsequent Examples. As used in the Reaction Schemes, the symbols R and Het are as previously defined, the symbol Tr represents trityl, i.e., triphenylmethyl, the symbol Ts represents tosyl, i.e. p-toluenesulfonyl or 4-methylbenzenesulfonyl, and the symbol Ph represents phenyl. The compounds obtained in the Reaction Schemes may be purified by conventional methods well known to the art, e.g. chromatography, recrystallization, etc.

The Formula I compounds have an asymmetric carbon atom at the C2-position in the glyceryl backbone and consequently they may exist in either the R or S optical isomeric forms (enantiomers) or as racemates. Substantially pure forms of the R- and S-isomers may be obtained, substantially free of the other, by the application of art-recognized resolution methodologies such as column chromatography using chiral columns, or by utilizing an appropriate R- or S-isomer of a precursor during synthesis. See, for example, the starting Compound (A) shown in Reaction Scheme I.

In addition, cis- and trans-geometric isomers may also be present in the subject compounds, e.g., when R in Formula I is $C_{1-130}$ alkenyl. Thus, by starting with an appropriate cis- or trans-precursor, the corresponding Formula I compound will be obtained.

All racemic and isomeric forms of the Formula I compounds, including pure enantiomeric and geometric isomers and mixtures thereof, are within the scope of this invention. Unless stated otherwise, the compounds of the following Examples are in racemic form.

Working up the individual stepwise products indicated in the following Reaction Schemes is advantageously carried out by standard methodologies, for example, by evaporating down the reaction solution or precipitating the product from the reaction solution by dilution with appropriate antisolvents. The crude intermediate products obtained may be quite suitable, without further purification, for the preparation of the final products, which then may be purified. Particularly suitable methods for purifying the Formula I compounds are conventional chromatographic methods such as preparative thin-layer chromatography (TLC), column chromatography, adsorption chromatography, medium pressure liquid chromatography (MPLC), high pressure liquid chromatography (HPLC) or kinetic resolution.

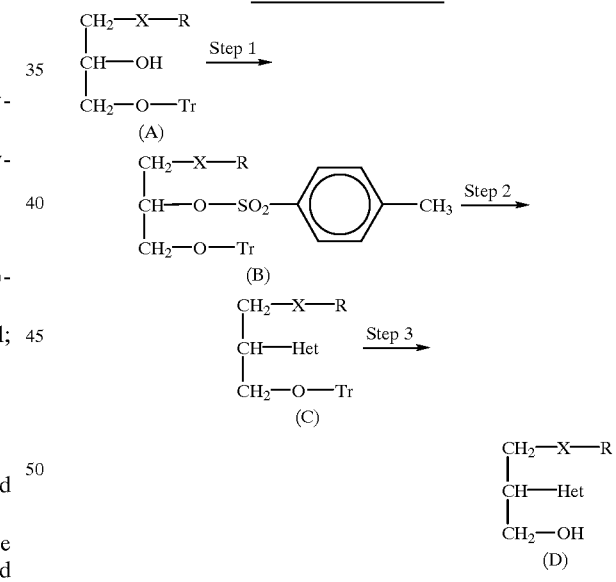

Step 1:

Compounds (A), which are known in the literature or are obtainable by art recognized procedures, for example, see A. Hermetter and F. Paltauf, Procedures for the Synthesis of Ether Lipids, p. 393 et.seq., in H. K. Mangold and F. Paltauf, Ether Lipids, Academic Press, 1983: and F. Paltauf and A. Hermetter, Methods Enzymol., (1991) 197, 134–149. A solution of (A) in an amphoteric aprotic solvent, e.g., pyridine, tetrahydrofuran, 1,4-dioxane, and the like, is added dropwise with stirring to a solution of a stoichiometric amount of p-toluenesulfonyl chloride, preferably in solution with the same solvent. The reaction mixture may be maintained at room temperature until the reaction is essentially completed. The reaction mixture is then subjected to conventional workup, for example, by extraction with appropriate organic solvents, aqueous washes, drying, solvent evaporation, recrystallization and the like, to yield the desired 2-O-p-toluenesulfonyl derivative (B).

Step 2:

Compound (B) is reacted with a stoichiometric amount of the desired Het-H compound in anhydrous dimethyl sulfoxide in the presence of sodium dimethyl-sulfinylmethide. Elevated temperatures are advantageously employed to enhance the rate of reaction, e.g. to about 100° C. After the reaction is completed, conventional workup yields the desired 2-Het derivative (C).

Step 3:

Removal of the trityl function in (C) to yield (D) is readily accomplished by art-recognized procedures, e.g., by reaction with boron trifluoride in an appropriate organic solvent such as methanol at reduced or ambient temperature, A. Hermetter and F. Paltauf, Chem. Phys. Lipids 29:191 (1981), followed by conventional workup.

REACTION SCHEMES 2a, 2b, & 2c

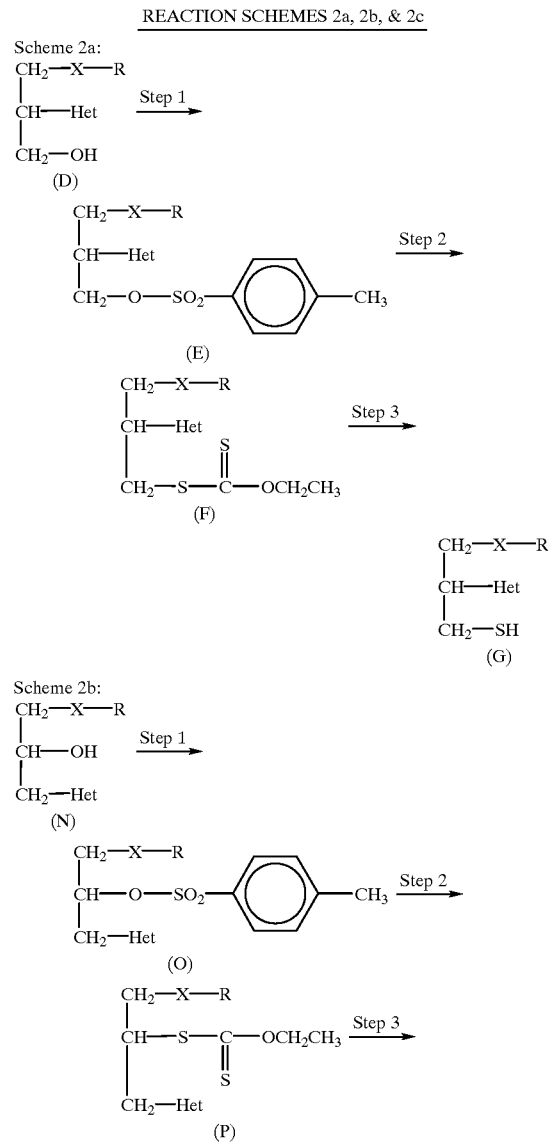

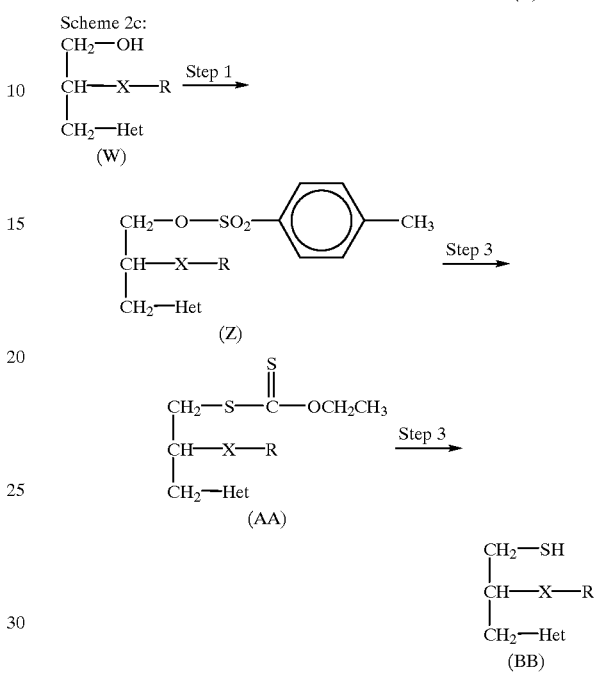

Reaction Schemes 2a, 2b, and 2c differ only in the positional isomerism of the starting compounds. The methodology is taken from S. Zalipsky et al., Int. J. Peptide Protein Res., (1987) 30: 740–783.

Step 1:

Compound (D) is prepared by the method described in Reaction Scheme 1. Compound (N) is prepared by the method described in Reaction Schemes 3 and 4 below. Compound (W) is prepared by the method of Reaction Scheme 6 below. A mixture of (D) or (N) or (W) and p-toluenesulfonyl chloride in 1:1 methylene chloride-pyridine is stirred at 25° C. for 24 h. After the reaction is completed, conventional workup yields the desired p-toluenesulfonate derivative (E)/(O)/(Z).

Step 2:

Conversion of the Ts moiety in (E)/(O)/(Z) to the O-ethylxanthate moiety in (F)/(P)/(AA): A mixture of (E) or (O) or (Z) and potassium O-ethylxanthate in deionized, degassed water is stirred at 25° C. for 24 h. After the reaction is completed, conventional workup yields the desired ethoxythiocarbonylthio derivative (F)/(P)/(AA).

Step 3:

Conversion of the ethoxythiocarbonylthio moiety in (F)/(P)/(AA) to the thiol moiety in (G)/(Q)/(BB): A mixture of Compound (F) or (P) or (AA) and 3 equivalents of glycine in deionized, degassed water is stirred at 25° C. for 24 h while maintaining the reaction mixture at pH 9.5 with gradual additions of a 2N aqueous NaOH solution. After the reaction is completed, the reaction mixture is brought to pH 3 by addition of 6N aqueous HCl followed by conventional workup to yield the desired thiol derivative (G)/(Q)/(BB).

REACTION SCHEME 3

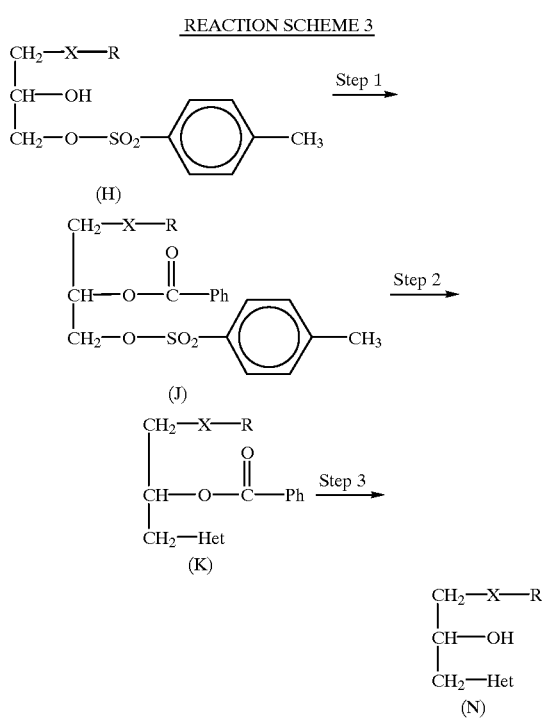

Step 1:

The compounds of Formula (H) are known or are obtainable by art recognized procedures, for example, see P. N. Guivisdalsky and R. Bittmann, J. Org. Chem., (1989) 54, 4637–4642. In general, the epoxide of glycidyl tosylate is opened in the presence of boron trifluoride catalyst for reaction with the aliphatic alcohol, ROH, in an aprotic solvent, e.g., chloroform, to yield (H).

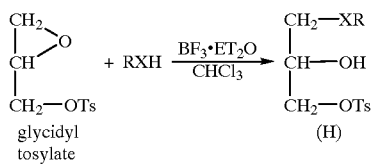

The individual R and S enantiomers and racemic forms of glycidyl tosylate are commercially available and, accordingly, can be used as starting materials for making the enantiomers or racemates of (H).

To avoid side reactions, the hydroxyl function of (H) is protected under mild conditions, for example, by conventional acylation with a stoichiometric excess of benzoyl chloride (Ph—COCl) in an appropriate aprotic solvent such as toluene, chloroform, or methylene chloride and an excess of a sterically hindered base such as N,N-diisopropylethylamine. The reaction should be carried out at a temperature ranging from room temperature to the boiling point of the chosen solvent. After completion of the reaction, conventional workup yields (J).

Step 2:

Compound (J) is reacted with a stoichiometric amount of the desired Het—H in anhydrous dimethyl sulfoxide in the presence of sodium dimethyl-sulfinylmethide. Elevated temperatures, e.g., about 100° C., are advantageously employed to enhance the rate of reaction. After the reaction is completed, conventional workup yields the desired 3-Het derivative (K).

Step 3:

Removal of the protecting benzoyl group is readily accomplished by saponification with an excess of a strong inorganic base such as sodium or potassium hydroxide in aqueous solution. The aqueous base is added to a solution of (K) in an appropriate amphoteric protic or aprotic solvent such as methanol, ethanol, isopropanol, pyridine, dioxane, and the like. After completion of the reaction, conventional workup yields the desired (N) compound.

REACTION SCHEME 4

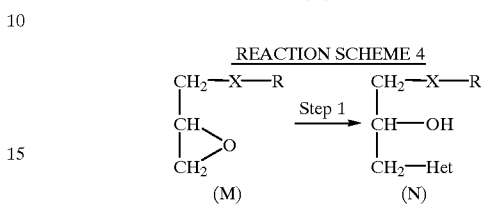

This Reaction Scheme provides an alternative and preferred procedure to Reaction Scheme 3.

Step 1:

The compounds (M) are commercially available or are obtainable by art-recognized procedures. See, for example, B. Cimetiere and J. M. Julia, Bull. Soc. Chim. Fr. (1991) 128:926–938; Rattay et al., Chem. Phys. Lipids (1995) 75:81–91; Bittman et al., J. Med. Chem. (1994) 37:425–430; W. Respond and J. Chlebicki, Polish Journal of Chemistry (1984) 58:1237–1242; and T. K. Todsen et al., J. Am. Chem. Soc., (1950) 72:4000–4002.

Conversion of (M) into (N) is accomplished by the method of Ueda et al., J. Heterocyl. Chem. (1971) 8:827–829. A mixture of (M), one equivalent of the appropriate Het-H compound and a catalytic amount of anhydrous potassium carbonate in an aprotic solvent such as di methyl formamide, dimethyl sulfoxide, or 1,2-dioxane is stirred at elevated temperatures, preferably at 60–90° C., for 12–48 hours under an inert atmosphere (nitrogen is preferred). After completion of the reaction, conventional workup yields (N).

REACTION SCHEME 5

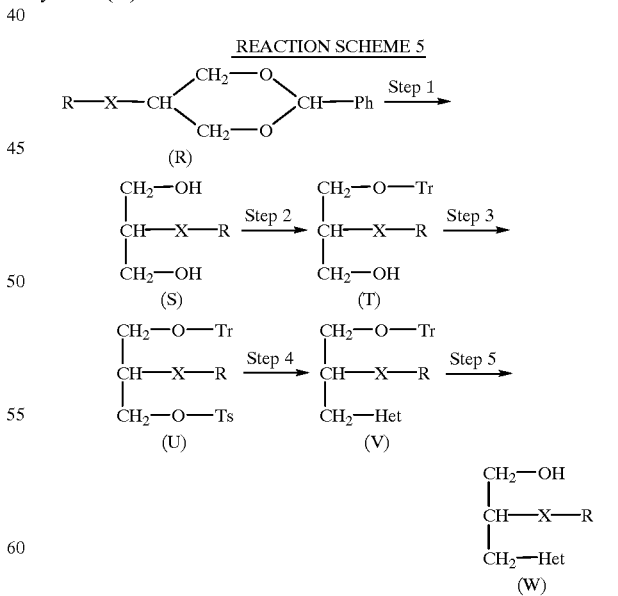

Step 1:

Compounds of Formula (R) are readily obtained from the known precursor 1,3-benzylidene-glycerol by introducing the R moiety analogously to the synthesis of 1-O-hexadecyl- 2,3-isopropylidene-glycerol as described by A. Hermetter and F. Paltauf (1983), supra.

Compounds (S) are commercially-available or readily obtainable from 2-OR-1,3-benzylideneglycerol by conventional acid-catalyzed hydrolysis of the benzylidene protective group (e.g., by treatment with hydrochloric acid in methanol), following procedures described in the literature. See, for example, E. O. Oswald et al., Lipids (1966) 1:121; and A. Hermetter and F. Paltauf (1983), supra.

Step 2:
Compound (S) is tritylated in conventional manner by reaction with triphenylmethyl chloride in an aprotic solvent under anhydrous conditions at room temperature. After completion of the reaction, conventional workup yields the desired trityl derivative (T).

Step 3:
A solution of (T) in an amphoteric aprotic solvent is added dropwise with stirring to a solution of p-toluenesulfonyl chloride, preferably in solution with the same solvent. The reaction mixture may be maintained at room temperature until the reaction is essentially completed, and then subjected to conventional workup to yield the desired tosyl derivative (U).

Step 4:
Replacement of the —O—Ts substituent in (U) with a Het moiety is readily accomplished by the reaction of (U) with the desired Het—H compound in anhydrous dimethyl sulfoxide in the presence of sodium dimethylsulfinyl methide, followed by conventional workup to yield the desired 1-Het derivative (V).

Step 5:
Removal of the trityl function in (V) to yield (W) is readily accomplished by art-recognized procedures.

REACTION SCHEME 6

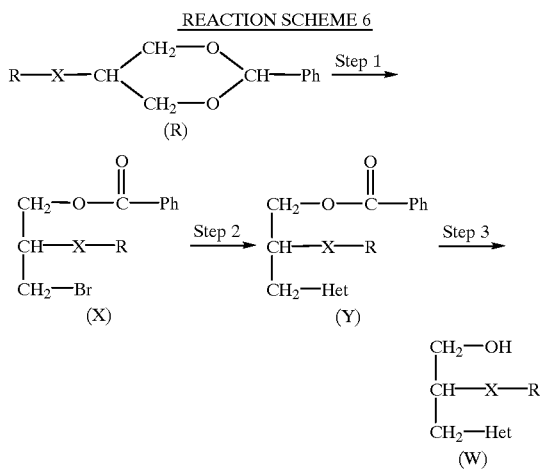

This Reaction Scheme provides an alternative procedure to Reaction Scheme 5.

Step 1:
Oxidative ring opening of (R) is carried out by treatment with a slight excess of N-bromosuccinimide (NBS) in carbon tetrachloride in the presence of excess barium carbonate. After the reaction is complete, conventional workup yields (X).

Step 2:
Compound (X) is reacted with the desired Het—H compound as described in Step 2 of Reaction Scheme I to yield the Het-substituted derivative (Y).

Step 3:
Debenzoylation of the protected hydroxyl function of (Y) is carried out as described for Compound (K) in Step 3 of Reaction Scheme 3 to yield (W).

UTILITY

The Formula I compounds, including the isomeric forms thereof, pharmaceutically-acceptable salts thereof, and isomeric forms of the salts, are useful antibacterial and antiviral agents for the prevention and treatment of bacterial and viral infections and are useful therapeutic agents for treating infections caused by bacteria and viruses in mammals.

A. ANTIBACTERIAL ACTIVITY

The antibacterial activity of the Formula I compounds and pharmaceutically-acceptable salts thereof are illustrated by the in vitro activity of Formula I compounds in inhibiting the growth of *Streptococcus pyogenes* and *Mycobacterium tuberculosis*.

In addition to *S. pyrogenes* and *M. tuberculosis*, infections caused by other bacteria, including *Escherichia coli, Pseudomonas aeruginosa, Streptococcus aureus, Streptococcus faecalis, Salmonella cholerasuis, Klebsiella pneumoniae, Pseudomonas aeruginosa, Proteus mirabilis, Enterococcus faecalis*, and *Helicobactor pylori*, may be prevented or treated by administration of the subject Formula I compounds and pharmaceutically-acceptable salts thereof.

The antibacterial compositions of the present invention are suitable for application to mammals, including human beings, horses, cattle, dogs and rodents. The route of administration is preferably oral or parenteral. Other administration routes, e.g., topical, buccal, or nasal administration, may also be used. Topical administration of the Formula I compounds or pharmaceutically-suitable salts thereof can be used for systemic treatment.

The daily dose and dosage regimen of the compounds may vary depending upon such factors as the bacteria involved in the infection, the species of mammal infected by the bacteria, the sex, age, body weight and general medical condition of the individual mammal being treated, the type of formulation or dosage form being administered, and the route of administration. The daily dose and dosage regimen are normally at the discretion of a medical or veterinary practitioner administering the treatment.

However, a suitable effective dose of the antibacterial agent is in the range of about 0.5 to about 500 mg/kg body weight per day, preferably in the range of about 1 to about 300 mg/kg body weight per day of one or more Formula I compounds. (If the agent is a salt of a Formula I compound, the dose is determined on the basis of the mass of the Formula I compound in the salt.) The total daily dose, for example, may be given as a single dose or multiple doses, e.g., two to six times per day, or by intravenous infusion for a selected duration. Dosages above or below the cited range are within the scope of the present invention and, as desired or determined to be necessary by the medical or veterinary professional, may be administered to a mammal being treated.

Effective unit dosage forms containing, for example, from about 0.5 to about 500 mg of one or more Formula I compounds (per se or as part of a pharmaceutically-acceptable salt) per unit dosage are suitably employed. As used herein, the term "effective unit dosage" or "effective unit dose" means a predetermined antibacterial amount sufficient to be effective against the bacterial organism in vivo, and "unit dosage form" includes a discrete dosage unit such as a capsule, bolus, tablet, metered dose, and the like.

The Formula I compounds are sparingly soluble in aqueous solutions at neutral pH. Accordingly, liquid formulations which account for this factor may be made according to art-recognized pharmaceutical techniques. Illustrative examples include an injectable formulation wherein the active compound is dissolved in a suitable solvent or co-solvent such as polyethylene glycol or propylene glycol, or a sealed gelatin capsule enclosing an oily solution of the active compound, or a suppository wherein the active compound(s) is dispersed in cocoa butter, or a liposome formulation. An exemplary liposome formulation is an active compound encapsulated in a glycerophospholipid liposome, such as phosphatidylcholine sonicated vesicle or multilamellar vesicle. In any event, the aforementioned characteristics of the Formula I compounds are not uncommon in the pharmaceutical area and, accordingly, art-recognized pharmaceutical techniques are employed to prepare appropriate formulation for such compounds as those of Formula I, isomers thereof, and pharmaceutically-acceptable salts of either.

1. ANTIBACTERIAL ASSAY OF MYCOBACTERIUM TUBERCULOSIS

Evidence for the antituberculosis activity of the Formula I compounds are shown by the results obtained in screening of the compounds against *Mycobacteriulm tuberculosis* strain H37Rv at the Tuberculosis Antimicrobial Acquisition and Coordinating Facility (TAACF) of the National Institute of Allergy and Infectious Diseases, Southern Research Institute, GWL Hansen's Disease Center, Colorado State University.

Table 1 shows the results of the inhibition assay. These results are expressed as the Minimum Inhibitory Concentration (MIC) which is the minimum concentration that inhibits at least 99% of the growth of *M. tuberculosis* strain H37Rv. Exposure of *M. tuberculosis* to compounds CPR 1004, CPR 1005 and CPR 1104 inhibits the colony growth relative to control. This represents a substantial antituberculosis effect at relatively low MIC values.

TABLE 1

| COMPOUND | MIC VERSUS H37Rv ($\mu$g/mL) |
|---|---|
| CPR 1004 | 12.5 |
| CPR 1005 | 6.25 |
| CPR 1104 | 1.6 |

2. ANTIBACTERIAL ASSAY OF STREPTOCOCCUS PYROGENES a. Tenfold dilutions of the Formula I compounds are made in sterile distilled water to obtain concentrations of 1000, 100, 10 and 1 $\mu$g/mL.

b. Molten Mueller-Hinton agar (MHA) is prepared and then cooled to 50° C.

c. Then, 5 mL of each dilution of Formula I compound (including the 10 mg/mL stock solution) are added to 45 mL of 50° C. MHA to achieve final concentrations of 1000, 10, 1, and 0.1 $\mu$g/mL.

d. Each flask is swirled immediately after addition of the Formula I compound, and the 50 mL agar-compound mixture is poured into a single large (150 mm) petri dish.

e. Control plates are also prepared: two with plain MHA and two with MHA containing 10% diluent (PEG 200-ethanol).

f. The plates are cooled to room temperature overnight.

g. Bacteria are grown overnight in Mueller-Hinton broth (MHB) and diluted with sterile saline to give a turbidity equal to a 0.5 McFarland standard. This is further diluted 1 part to 50 parts sterile saline.

h. Each large plate is divided into seven wedge-shaped areas; one wedge is utilized for each isolate.

i. Three 10 mL volumes of each isolate is pipetted onto its area on each plate. The plates are incubated overnight for 48 hr, and the presence or absence of growth is recorded.

Table 2 shows the results of the inhibition assay. Exposure of *S. pyrogenes* colony to compounds CPR 1004 and CPR 1005 inhibited the colony growth relative to the controls. This represents a substantial antibacterial effect of the Formula I compounds on the growth of *S. pyrogenes* at relatively low MIC values.

TABLE 2

| COMPOUND | MIC ($\mu$g/mL) |
|---|---|
| CPR 1004 | 1 |
| CPR 1005 | 10 |

The invention thus provides a method of treating a bacterial infection in a mammal afflicted with the same comprising administering to the mammal an antibacterial-effective amount of a Formula I compound or a pharmaceutically acceptable salt thereof. The invention also provides pharmaceutical compositions comprising an antibacterial-effective amount of a Formula I compound, or a pharmaceutically acceptable salt thereof, in combination with a pharmaceutically-acceptable carrier.

B. ANTIVIRAL ACTIVITY

The antiviral activity of the Formula I compounds and pharmaceutically-acceptable salts thereof may be assayed by many ways conventional in the art. Two of these assays are described here. The first assay measures inhibition of cytopathic effects (CPE) caused by viral infection of cells, and the second assay is a standard viral yield reduction assay. This yield reduction assay is a modification of the general method described by Erlich et al., Ann. N.Y. Acad. Sci. (1965) 130: 5–16. These two assays demonstrate the marked antiviral activity of the subject compounds and their pharmaceutically-acceptable salts.

No cytotoxicity has been observed with the compounds of Formula I or pharmaceutically-acceptable salts thereof at antiviral-effective levels.

The antiviral agents of the present invention (the compounds of Formula I and the pharmaceutically-acceptable salts thereof) are particularly effective for the treatment of an infection by Poliomyelitis virus (including all three immunologically distinguishable types thereof), and Respiratory Syncytial virus, although infections caused by other viruses, such as Varicella-Zoster virus, Togaviruses, Cytomegalovirus (CMV), Epstein-Barr virus (EBV), Picornaviruses, Rhinovirus, Human papilloma viruses and Hepatitis viruses, among others, may also be effectively treated.

The antiviral agents of the present invention are suitable for application to mammals (such as human beings, horses, cattle, dogs and rodents). The route of administration is preferably oral or parental, although it is possible to administer the antiviral agents by other administration routes, e.g., by topical application, depending on whether the preparation is used to treat internal or external viral infections, or nasal application. Topical application can be used for systemic treatment.

The daily dose and dosage regimen may vary depending upon the virus involved in the infection, the species of mammal infected by the virus, the sex, age, body weight and general medical condition of the individual mammal being treated, the Formula I compound, formulation, or dosage form being administered, and the route of administration. The daily dose and dosage regimen are ultimately at the discretion of the medical or veterinary practitioner administering the treatment.

However, a suitable effective dose of the antiviral agent is in the range of about 0.5 to about 500 mg/kg body weight per day, preferably in the range of about 1 to about 300 mg/kg body weight per day, of one or more Formula I compounds. (If the agent is a salt of a Formula I compound, the dose is determined on the basis of the mass of the Formula I compound in the salt.) The total daily dose, for example, may be given as a single dose or multiple doses, e.g., two to six times per day, or by intravenous infusion for a selected duration. Dosages above or below the cited range are within the scope of the present invention and, as desired or determined to be necessary by the medical or veterinary professional, may be administered to a mammal being treated.

Effective unit dosage forms containing, for example, from about 0.5 to about 500 mg of compound of Formula I (per se or as part of a pharmaceutically-acceptable salt) per unit dosage are suitably employed. As used herein, the term "effective unit dosage" or "effective unit dose" means a predetermined antiviral amount of one or more Formula I compounds sufficient to be effective against the virus in vivo, and "unit dosage form" includes a discrete dosage unit such as a capsule, bolus, tablet, metered dose, and the like.

1. ANTIVIRAL ASSAY OF POLIOVIRUS a. Buffalo Green Monkey Kidney Cells (ATCC CCL 81) were plated at a density of $7 \times 10^4$ cells per well in a standard flat bottom 96-well microtiter plate. The cells are contained in a volume of 200 mL Dulbecco's Modified Eagles Medium (DMEM) containing 10% serum (1:1 mixture of fetal bovine serum and defined supplemented calf serum (Hyclone, Inc., Ogden, Utah), 10 mM HEPES buffer (pH 7.2), 100 U/mL penicillin and 100 mg/mL streptomycin sulfate). HEPES and antibiotics were obtained from Sigma Chemical Co. (St. Louis, Mo.). Two wells are plated for each of the following samples: A Formula I compound, cell control (cells only), virus control (cells infected with the virus but not treated), vehicle control (solvent, 9:1 dimethylsulfoxide:ethanol), and cell counts.

b. The cultures were incubated at 37° C., 5% $CO_2$, 100% humidity, until a monolayer of cells is formed on the bottom of each well (usually overnight).

c. The media is removed from the wells by aspiration. The wells are replenished with either media containing the desired concentration of test compound (100 mM final concentration), media only (cell control and virus control samples), or solvent (9:1, dimethylsulfoxide:ethanol) at a final concentration of 0.33%. Active compounds are dissolved at a stock concentration of 30 mM and diluted 300-fold. The cell count wells receive media only.

d. The cultures are incubated for 24 hr under standard conditions.

e. At the end of 24 hr, each well is scored for the presence of toxicity (cells exposed to compound but not infected) as indicated by rounding and/or detachment of the cells from the plate. Scoring is as follows:

±None of the cells rounded
1+<25% of cells rounded
2+25 to 50% of the cells rounded
3+75% of the cells rounded
4+100% of the cells rounded.

f. The media is removed from the cell count wells by aspiration. The monolayer is rinsed 2× with 100 mL of trypsin:ethylene diamine tetraacetic acid (EDTA) solution and is incubated at 37° C. until the cells could be suspended (usually about 2 to 5 minutes). The cells are counted in a hemocytometer to determine the number of cells per well.

g. The cells are then infected. For this study, the Poliovirus Type III vaccine strain (ATCC VR 300) was used. The cells are infected as follows. The media is aspirated and replaced with 50 mL of media (2% serum) containing 100 TCID50 doses of Poliovirus Type III. The cultures are then incubated at 37° C., 5% $CO_2$ for 60 minutes. The plate is gently shaken at 15 minute intervals to ensure adequate distribution of the virus and exposure of the cells to the virus. At the end of the incubation period, the excess viral solution is removed by aspiration, and the wells are replenished (200 µL/well) with either media containing 2% serum (cell control and virus control samples), media containing 2% serum and a Formula I compound, or media containing the vehicle (solvent control) at the same concentrations as in the test compound wells.

h. The plate is incubated at 37° C. for 48 hr.

i. At the end of 48 hr, each well is scored for the presence of CPE as indicated by rounding and/or detachment of the cells from the plate. Scoring is as described above.

j. After scoring for viral CPE, the yield of infectious virus in each well is measured by standard plaque assay on Vero cells (ATCC CCL 81). Virus is released from the cells by freezing and thawing (−80° C. to 37° C.) three times. Serial 10-fold dilutions of each sample are made in media containing 2% serum. Vero cell monolayers of Buffalo Green monkey kidney cells in 96-well microtiter plates ($1 \times 10^6$ cells/well) are infected with 100 mL of each dilution (separate well per dilution). Following a 1 hour adsorption period with gentle rocking at 37° C., the virus inoculum is removed, the monolayer is overlaid with 2 mL of 2% methylcellulose in media with 2% serum, followed by 2 mL of media with 2% serum. The microtiter plates are incubated at 37° C. until viral plaques became visible (3–4 days). The cells are fixed by adding 2 mL of phosphate-buffered saline (PBS) containing 10% (v/v) formalin. The methylcellulose, media, and formalin were removed by aspiration. Two mL of PBS-formalin are added and the plates incubated for 5 minutes. The fixative is removed, and the cells stained with 1 % crystal violet in 70% ethanol-water (v/v). Excess stain is rinsed from the cells, the number of plaques is counted, and the yield of virus in the original sample is calculated.

Table 3 shows the results of the CPE inhibition assay. Exposure of separate cells to the compounds CPR 1004 and CPR 1005 inhibited the development of viral cytopathic effect. These compounds are not toxic at the concentrations tested. The dimethyl sulfoxide vehicle used for dissolving the Formula I compounds is not toxic and does not prevent the development of viral CPE, indicating that the vehicle itself has no antiviral activity. The cell control and virus controls also display the expected results. Table 3 also shows the data from the yield reduction assay. Compounds CPR 1004 and CPR 1005 reduced the yield of infectious virus by 41.7-fold and $1.03 \times 10^4$-fold, respectively, compared to the virus control. Clearly, the subject compounds display substantial antiviral activity.

TABLE 3

| SAMPLE | TOXICITY | VIRAL CPE | VIRUS YIELD (PFU/mL) | VIRUS YIELD (YIELD) | FOLD-REDUCTION[c] |
|---|---|---|---|---|---|
| Cell Control | N[a] | —[b] | — | — | — |
| Vehicle Control (DMSO/Ethanol) | N | 4+ | $2.9 \times 10^7$ | 1.00 | 0 |
| Virus Control | — | 4+ | $2.9 \times 10^7$ | 1.00 | 0 |
| CPR 1004 | N | ± | $7.0 \times 10^5$ | 0.024 | 41.7 |
| CPR 1005 | N | 1+ | $2.8 \times 10^3$ | $9.65 \times 10^{-5}$ | $1.03 \times 10^4$ |

[a]N = Not Toxic
[b]Not scored
[c]Virus control/test compound

2. ANTIVIRAL ASSAY OF RESPIRATORY SYNCYTIAL VIRUS a. HEP 2 Cells (ATCC HB 8065) are plated at a density of $7 \times 10^4$ cells per well in a standard flat-bottom 96-well microtiter plate. The cells are contained in a volume of 200 mL Dulbecco's Modified Eagles Medium (DMEM) containing 10% serum (1:1 mixture of fetal bovine serum and defmed supplemented calf serum (Hyclone, Inc., Ogden, Utah), 10 mM HEPES buffer (pH 7.2), 100 U/mL penicillin and 100 mg/mL streptomycin sulfate). The wells are plated as described in paragraph B. 1. a., above b. The cultures are incubated under standard conditions until a monolayer of cells is formed on the bottom of each well (usually overnight).

c. The media is removed from the wells by aspiration. The wells are refilled with either media containing the desired concentration of a Formula I compound (100 mM final concentration), media only (cell control and virus control samples), or solvent (9:1, dimethylsulfoxide:ethanol) at a final concentration of 0.33%. Formula I compound are dissolved at a stock concentration of 30 mM and diluted 300-fold. The cell count wells receive media only.

d. The cultures are incubated for 24 hr.

e. At the end of 24 hr, each well is scored for the presence of toxicity (cells exposed to compound but not infected) as indicated by rounding and/or detachment of the cells from the plate. Scoring is as described above.

f. The media is removed from the cell count wells by aspiration. The monolayer is rinsed 2× with 100 mL of trypsin:ethylene diamine tetraacetic acid (EDTA) solution and was incubated at 37° C. until the cells could be suspended (usually 2–5 minutes). The cells are counted in a hemocytometer to determine the number of cells per well.

g. The remaining wells, except the cell control samples, are infected with 2 plaque forming units per cell of the standard Respiratory Syncytial Virus (RSV, strain Long) using the following procedure. The media is aspirated from the wells. Media (50 mL) with 2% serum containing the desired amount of virus is added to each well. The cultures are then incubated for 60 minutes. The plate is gently shaken at 15 to 30 minute intervals to ensure adequate distribution of the virus and exposure of the cells to the virus. At the end of the incubation period, the excess viral solution is removed by aspiration, and the wells are replenished (200 mL/well) with either media containing 2% serum (cell control and virus control samples), media containing 2% serum and compound, or media containing the vehicle (solvent control) at the same concentration in the test compound wells.

h. The plate is incubated for 48 hours.

i. At the end of 48 hours, each well is scored for the presence of CPE as indicated by rounding and/or detachment of the cells from the plate. Scoring is as described above.

j. After scoring for viral CPE, the yield of infectious virus in each well is measured by standard plaque assay on Vero cells, as described above.

Table 4 shows the results of the CPE inhibition assay. Exposure of the cells to CPR 1005 inhibits the development of viral cytopathic effect. Again, the compound is not toxic at the dosages tested.

TABLE 4

| SAMPLE | FINAL CONCENTRATION (mM) | TOXICITY | VIRAL CPE |
|---|---|---|---|
| Cell Control | NA[a] | N[b] | —[c] |
| Vehicle Control (DMSO/Ethanol) | NA | N | 4+ |
| Virus Control | NA | — | 4+ |
| CPR 1005 | 100 | N | 2+ |

[a]Not applicable
[b]N = Not Toxic
[c]Not scored

The invention thus provides a method of treating a viral infection in a mammal afflicted with the same, comprising administering to the mammal an antiviral-effective amount of a Formula I compound or a pharmaceutically acceptable salt thereof. The invention also provides pharmaceutical compositions comprising an antiviral-effective amount of a Formula I compound, or a pharmaceutically-acceptable salt thereof, in combination with a pharmaceutically-acceptable carrier.

FORMULATIONS

Pharmaceutical formulations of the present invention comprise an active compound(s), i.e. a Formula I compound (s) or salt thereof, together with a pharmaceutically-acceptable carrier therefor and optionally other therapeutically-active ingredients. The carrier must be pharmaceutically-acceptable in the sense of being compatible with the other ingredients of the formulation and not deleterious to the recipient thereof.

The present invention is further drawn to a pharmaceutical formulation comprising a one or more Formula I compounds in combination with a pharmaceutically-acceptable carrier thereof.

The formulations include those suitable for oral, topical, rectal or parenteral (including subcutaneous, intramuscular and intravenous) administration. Preferred are those suitable for oral or topical administration.

The Formula I compounds have relatively low melting points which should be taken into consideration, for example, in preparing tablets on a commercial scale where the heat of compression may be a factor. And, as noted above, the Formula I compounds are also rather insoluble in neutral aqueous solutions.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as a suspension, solution, syrup, elixir, emulsion, dispersion, and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient.

Useful formulations also comprise concentrated solutions or solids containing one or more Formula I compounds which upon dilution with an appropriate solvent give a solution suitable for parenteral administration.

Preparations for topical or local applications, which are, for example, antiviral or for antibacterial usage, comprise aerosol sprays, lotions, gels, ointments, etc. and pharmaceutically-acceptable vehicles therefore such as lower aliphatic alcohols, polyglycerols, esters of fatty acids, oils and fats, silicones, and other conventional topical carriers.

In topical formulations, the Formula I compounds are preferably utilized at concentrations of from about 0.1% to about 5.0% percent by weight.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The amount of Formula I compound required to be effective for the indicated activity will, of course, vary with the individual mammal being treated and is ultimately at the discretion of the medical or veterinary practitioner, as noted above. A suitable effective dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be from about 75 to about 7500 mg per day, and a typical dose would be about 800 mg per day. If discrete multiple doses are indicated, treatment might typically be 200 mg of a Formula I compound given 4 times per day.

EXAMPLES

The following Examples are provided solely to provide a more complete understanding of the present invention. The Examples do not limit the scope of the invention described and claimed herein in any fashion. The Examples include alphabetical references to the Reaction Schemes described above.

Example 1

A. 1-O-Octadecyl-2-O-p-toluenesulfonyl-3-O-tritylglycerol

A solution of 1-O-octadecyl-3-O-trityl-glycerol (173.51 g, 295.63 mmol) in 895 mL water-free pyridine is added dropwise to a solution of p-toluenesulfonyl chloride (88.49 g, 464.15 mmol) in 670 mL water-free pyridine with constant stirring. The reaction mixture is kept at ambient temperature (20–23° C.) for two days. Diethyl ether (2.8 L) is added, and the organic phase is washed six times with water, twice with 0.5 N HCl (500 mL each), twice with diluted aqueous sodium carbonate, and then washed with water until neutral. After drying the organic phase over sodium sulfate, the solvent is removed under vacuum. The residue is triturated with isopropanol (1140 mL) with stirring until the product crystallizes. After cooling to 4° C., the product, 1-O-octadecyl-2-O-p-toluenesulfonyl-3-O-tritylglycerol, is isolated by filtration, washed with isopropanol and dried under vacuum. Yield: 190.14 g (86.91%); m.p. 56–58° C.; $R_f$ value (TLC on silica gel 60) of 0.38 with benzene as the developing solvent; and $R_f$ value of 0.74 with benzene/methanol (50/2).

B. Following the procedure of Example 1-A using an equivalent amount of 1-O-hexadecyl-3-O-trityl-glycerol as the starting Formula (A) Compound yields as a final product the corresponding 1-O-hexadecyl-2-O-p-toluenesulfonyl-3-O-trityl-glycerol; yield 73%; $R_f$ value: 0.37 benzene; 0.79 benzene/methanol (50/2).

Example 2

The procedure of Example 1-A is followed except that an equivalent amount of the appropriate 1-O-R-3-O-trityl-glycerol is utilized as the starting Formula (A) compound to yield the following respective Formula (B) compounds:

1-O-eicosyl-2-O-p-toluenesulfonyl-3-O-trityl-glycerol;

S-1-O-octadecyl-2-O-p-toluenesulfonyl-3-O-trityl-glycerol;

1-O-(1-methylheptadecyl)-2-O-p-toluenesulfonyl-3-O-trityl-glycerol;

1-O-tetradecyl-2-O-p-toluenesulfonyl-3-O-trityl-glycerol;

R-1-O-hexadecyl-2-O-p-toluenesulfonyl-3-O-trityl-glycerol;

1-O-(cis-9-octadecenyl)-2-O-p-toluenesulfonyl-3-O-trityl-glycerol; and

1-O-(trans-8-hexadecenyl)-2-O-p-toluenesulfonyl-3-O-trityl-glycerol.

Example 3

A. 1-O-Octadecyl-2-(1-imidazolyl)-2-deoxy-3-O-trityl-glycerol

1-O-Octadecyl-2-p-toluenesulfonyl-3-O-trityl-glycerol (106.56 g, 144 mmol) and imidazole (29.28 g, 430 mmol) are dissolved in water-free dimethyl sulfoxide (800 mL) at 100° C. A solution of sodium dimethylsulfinylmethide, prepared from metallic sodium (6.72 g) in 800 mL dimethyl sulfoxide, is added and the resultant mixture is stirred at 100° C. for 72 hours. After cooling, diethyl ether (2000 mL) is added. The organic phase is washed six times with water (1500 mL each) and dried over sodium sulfate. The solvent is removed under vacuum.

The thus-obtained crude product (87.6 g), consisting of starting material and the desired product, according to thin layer chromatography (TLC) analysis, is purified by medium pressure liquid chromatography (MPLC). A solution of the crude product (0.6 g) in methylene chloride (2.0 mL) is applied onto a MPLC-column (30×3 cm) filled with silica gel 35–70 with the following parameters: pressure-0.9 atmosphere; flow rate-500 mL/hour; solvent-methylene chloride (fractions 1–35) and methylene chloride/methanol (40/2 v/v); fraction volumes of 10–15 mL are collected; yield is about 60%; purified 1-O-octadecyl-2-(1-imidazolyl)-2-deoxy-3-O-trityl-glycerol; m.p. 53–58° C.; $R_f$ value: 0.30 benzene/methanol 50/5.

MPLC purification of a larger amount of the crude product (1.85 g) in 3 mL methylene chloride/diethyl ether (40/2.5 v/v) is also carried out using a 40×4 cm column (pressure-0.9 atmosphere, flow rate-700 mL/hr).

B. The procedure of Example 3-A is followed, except that an equivalent amount of 1,2,4-triazole is substituted for the imidazole used therein, to yield as final product (oily liquid) the corresponding 1-O-octadecyl-2-(1-triazolyl)-2-deoxy-3-O-trityl-glycerol; $R_f$ value: 0.31 methylene chloride/ether 3/1; yield 83% after purification by column chromatography.

C. By following the procedure of Example 3-A, except that an equivalent amount of 1-O-hexadecyl-2-O-p-toluenesulfonyl-3-O-trityl-glycerol is utilized as the starting Formula (B) compound, there is obtained as final product the corresponding 1-O-hexadecyl-2-(1-imidazolyl)-2-deoxy-3-O-trityl-glycerol; $R_f$ value: 0.29 toluene/methanol 50/3; yield 45% after purification by column chromatography.

Example 4

The procedure of Example 3-A is followed except that an equivalent amount of each of the appropriate Formula (B) compounds and the appropriate Het-Compounds are utilized as the initial reactants to yield the following Formula (C) compounds as final products:

1-O-eicosyl-2-(1-imidazolyl)-2-deoxy-3-O-trityl-glycerol;

S-1-O-octadecyl-2-(1-imidazolyl)-2-deoxy-3-O-trityl-glycerol;

1-O-(1-methylheptadecyl)-2-(1-pyrrolyl)-2-deoxy-3-O-trityl-glycerol;

1-O-tetradecyl-2-(1-benztriazolyl)-2-deoxy-3-O-trityl-glycerol;

R-1-O-hexadecyl-2-(1-imidazolyl)-2-deoxy-3-O-trityl-glycerol;

1-O-(cis-9-octadecenyl)-2-(1-pyrazolyl)-2-deoxy-3-O-trityl-glycerol; and

1-O-(trans-8-hexadecenyl)-2-(1-indolyl) -2-deoxy-3-O-trityl-glycerol.

Example 5

A. 1-O-Octadecyl-2-(1-imidazolyl)-2-deoxy-glycerol

A solution of boron trifluoride (50%) in methanol (88 mL) is added to a solution of 1-O-octadecyl-2-(1-imidazolyl)-2-deoxy-3-O-trityl-glycerol (87.6 g, 137.52 mmol) in methylene chloride (2000 mL) and the resultant dark green solution is kept at ambient temperature for 24 hours. After washing with water (500 mL) the color changes to yellow. The resulting emulsion is separated into two phases by the addition of sodium chloride. The organic phase is washed consecutively with diluted aqueous sodium carbonate and water until neutral. After drying over sodium sulfate, the solvent is removed under vacuum. The thus-obtained crude 1-O-octadecyl-2-(1-imidazolyl)-2-deoxy-glycerol is purified by column chromatography as follows:

column: Prep 500 (Waters) silica;

solvent: methylene chloride/methanol/conc. ammonia 40/3.5/0.1 v/v/v;

pressure: 13 bar;

flow rate: 200–250 mL/hr;

yield: 19.3 g (35.7%);

m.p.: 56–58° C.;

$R_f$ value: 0.21 $CH_2Cl_2/CH_3OH$/c.$NH_3$ 40/3.5/0.1 v/v/v; 0.38 benzene/methanol 45/5.

B. By following the procedure of Example 5-A, except that an equivalent amount each of the 2-(1-triazolyl) and the 2-(1-imidazolyl) derivatives from Examples 3-B and 3-C, respectively, is utilized as the starting Formula (C) compound, the following respective final products are obtained: 1-O-octadecyl-2-(1-triazolyl)-2-deoxy-glycerol; m.p. 73–78° C.; $R_f$ value: 0.42 methylene chloride/methanol 45/5; 0.13 benzene/methanol 50/5; yield 83% after purification by column chromatography; and 1-O-hexadecyl-2-(1-imidazolyl)-2-deoxy-glycerol; m.p. 52–56° C.; $R_f$ value: 0.50 methylene chloride/methanol/water 40/15/1.5; yield 79% after purification by column chromatography.

Example 6

The procedure of Example 5-A is followed, except that an equivalent amount of each of the Formula (C) compounds from Example 4 is substituted for the 1-O-octadecyl-2-(1-imidazolyl)-2-deoxy-3-O-trityl-glycerol of Example 5-A, to yield the following respective Formula (D) compounds:

1-O-eicosyl-2-(1-imidazolyl)-2-deoxy-glycerol;

S-1-O-octadecyl-2-(1-imidazolyl)-2-deoxy-glycerol;

1-O-(1-methylheptadecyl)-2-(1-pyrrolyl)-2-deoxy-glycerol;

1-O-tetradecyl-2-(1-benztriazolyl)-2-deoxy-glycerol;

R-1-O-hexadecyl-2-(1-imidazolyl)-2-deoxy-glycerol;

1-O-(cis-9-octadecenyl)-2-(1-pyrazolyl)-2-deoxy-glycerol; and

1-O-(trans-8-hexadecenyl)-2-(1-indolyl)-2-deoxy-glycerol.

Example 7

1-O-Octadecyl-2-(1-imidazolyl)-2-deoxy-3-O-p-toluenesulfonyl-glycerol

A mixture of 1-O-octadecyl-2-(1-imidazolyl)-2-deoxy-glycerol (10.0 g, 0.025 mol) and p-toluenesulfonyl chloride (47.7 g, 0.25 mol) in anhydrous 1:1 $CH_2Cl_2$-pyridine is stirred at 25° C. under nitrogen for 24 hours. The resultant mixture is filtered, concentrated in vacuo and recrystallized three times from ethanol-acetone to provide product.

Example 8

By following the procedure of Example 7, except that an equivalent amount of each of the appropriate Formula (D) compounds of Example 6 are utilized as the initial reactant, the following respective final products of Formula (E) are obtained.

1-O-eicosyl-2-(1-imidazolyl)-2-deoxy-3-O-p-toluenesulfonate-glycerol;

S-1-O-octadecyl-2-(1-imidazolyl)-2-deoxy-3-O-p-toluenesulfonate-glycerol;

1-O-(1-methylheptadecyl)-2-pyrrolyl-2-deoxy-3-O-p-toluenesulfonate-glycerol;

1-O-tetradecyl-2-(1-benztriazolyl)-2-deoxy-3-O-p-toluenesulfonate-glycerol;

R-1-O-hexadecyl-2-(1-imidazolyl)-2-deoxy-3-O-p-toluenesulfonate-glycerol;

1-O-(cis-9-octadecenyl)-2-(1-pyrazolyl)-2-deoxy-3-O-p-toluenesulfonate-glycerol; and 1-O-(trans-8-hexadecenyl)-2-(1-indolyl)-2-deoxy-3-O-p-toluenesulfonate-glycerol.

Example 9

1-O-Octadecyl-2-(1-imidazolyl)-2-deoxy-3-ethoxythiocarbonylthio-3-deoxy-glycerol A mixture of 1-O-octadecyl-2-(1-imidazolyl)-2-deoxy-3-O-p-toluenesulfonyl-glycerol (8.0 g, 0.0146 mol) and potassium O-ethylxanthate (7.02 g, 0.0438 mol) in deionized, degassed water 85 mL) is stirred at 25° C. for 24 h under a nitrogen atmosphere. The resultant mixture is concentrated in vacuo and then extracted with 1:1 $CH_2Cl_2$-ethyl acetate (500 mL). The organic extracts are dried over $MgSO_4$, gravity filtered and concentrated in vacuo to a 45 mL volume. The resultant solution is added to cold ether 300 mL to provide the product as a white powder.

Example 10

By following the procedure of Example 9, except that an equivalent amount each of the appropriate Formula (E) compounds of Example 8 are utilized as the initial reactant, the following respective final products of Formula (F) are obtained.

1-O-eicosyl-2-(1-imidazolyl)-2-deoxy-3-ethoxythiocarbonylthio-3-deoxy-glycerol;

S-1-O-octadecyl-2-(1-imidazolyl)-2-deoxy-3-ethoxythiocarbonylthio-3-deoxy-glycerol;

1-O-(1-methylheptadecyl)-2-(1-pyrrolyl)-2-deoxy-3-ethoxythiocarbonylthio-3-deoxy-glycerol;

1-O-tetradecyl-2-(1-benztriazolyl)-2-deoxy-3-ethoxythiocarbonylthio-3-deoxy-glycerol;

R-1-O-hexadecyl-2-(1-imidazolyl)-2-deoxy-3-ethoxythiocarbonylthio-3-deoxy-glycerol;

1-O-(cis-9-octadecenyl)-2-(1-pyrazolyl)-2-deoxy-3-ethoxythiocarbonylthio-3-deoxy-glycerol; and 1-O-(trans-8-hexadecenyl)-2-(1-indolyl)-2-deoxy-3-ethoxythiocarbonylthio-3-deoxy-glycerol.

Example 11

1-O-Octadecyl-2-(1-imidazolyl)-2-deoxy-3-thiol-3-deoxy-glycerol

A mixture of 1-O-octadecyl-2-(1-imidazolyl)-2-deoxy-3-ethoxythiocarbonyl-thio-glycerol (5.0 g, 0.0106 mol) and glycine (2.39, 0.0318 mol) in deionized, degassed water (21 mL) is stirred at 25° C. for 30 min. during which the reaction mixture is maintained at pH 9.5 by periodic addition of 2N aqueous NaOH (10.6 mL total). The reaction mixture is then brought to pH 3 by addition of 6N aqueous HCl (5.5 mL) and then concentrated in vacuo. The resultant residue is dissolved into methylene chloride (85 mL), and the resultant methylene chloride solution is slowly poured into cold ether. The product which precipitates is collected by filtration, washed with ether and dried in vacuo to provide product.

Example 12

By following the procedure of Example 11, except that an equivalent amount of each of the appropriate Formula (F) compounds of Example 10 are utilized as the initial reactant, the following respective final products of Formula (G) are obtained.

1-O-eicosyl-2-(1-imidazolyl)-2-deoxy-3-thiol-3-deoxy-glycerol;

S-1-O-octadecyl-2-(1-imidazolyl)-2-deoxy-3-thiol-3-deoxy-glycerol;

1-O-(1-methylheptadecyl)-2-(1-pyrrolyl)-2-deoxy-3-thiol-3-deoxy-glycerol;

1-O-tetradecyl-2-(1-benztriazolyl)-2-deoxy-3-thiol-3-deoxy-glycerol;

R-1-O-hexadecyl-2-(1-imidazolyl)-2-deoxy-3-thiol-3-deoxy-glycerol;

1-O-(cis-9-octadecenyl)-2-(1-pyrazolyl)-2-deoxy-3-thiol-3-deoxy-glycerol; and

1-O-(trans-8-hexadecenyl)-2-(1-indolyl)-2-deoxy-3-thiol-3-deoxy-glycerol.

Example 13

1-O-Octadecyl-2-O-benzoyl-3-O-p-toluenesulfonyl-glycerol 9.98 Grams (20 mmol) of compound (H) with R being $C_{18}H_{37}$ is dissolved in 150 mL dry toluene. 3.88 Grams (30 mmol) of N,N-diisopropylethylamine is added followed by a solution of 4.19 g (30 mmol) of benzoyl chloride in 50 mL toluene within 10 minutes. The clear reaction mixture is allowed to stand 48 hours at room temperature, washed with water, washed twice with saturated sodium bicarbonate solution, again with water, dried over sodium sulfate, filtered and evaporated to dryness. The residual waxy solid (12.2 g) of 1-O-octadecyl-2-O-benzoyl-3-O-p-toluenesulfonyl-glycerol is used without further purification in the succeeding step.

Example 14

The procedure of Example 13 is followed, except that an equivalent amount of the appropriate Formula (H) compound is utilized as the initial reactant, to yield the following respective Formula (J) compounds:

1-O-tetradecyl-2-O-benzoyl-3-O-p-toluenesulfonyl-glycerol;

1-O-hexadecyl-2-O-benzoyl-3-O-p-toluenesulfonyl-glycerol;

1-O-eicosyl-2-O-benzoyl-3-O-p-toluenesulfonyl-glycerol;

S-1-O-octadecyl-2-O-benzoyl-3-O-p-tol uenesulfonyl-glycerol; and

R-1-O-hexadecyl-2-O-benzoyl-3-O-p-toluenesulfonyl-glycerol.

Example 15
1-O-Octadecyl-2-O-benzoyl-3-(1-triazolyl)-3-deoxy-glycerol 12.2 Grams (approximately 20 mmol) of the waxy solid obtained in Example 13 is reacted with the Het-compound, triazole, under the same reaction conditions and molar ratios as described in Step 2 of Reaction Scheme 1. After purification by column chromatography (400 g silica gel; toluene as the mobile phase), about 5.37 g (53.73% theoretical yield) of 1-O-octadecyl-2-O-benzoyl-3-(1-triazolyl)-3-deoxy-glycerol is obtained: $R_f$ value of 0.65; silica gel; methylene chloride/methanol 45/5.

Example 16

By following the procedure of Example 15, except that an equivalent amount of each of the appropriate Formula (J) compounds of Example 14 and the appropriate Het-compounds are utilized as the initial reactants, the following respective final products of Formula (K) are obtained.

1-O-tetradecyl-2-O-benzoyl-3-(1-imidazolyl)-3-deoxy-glycerol;

1-O-hexadecyl-2-O-benzoyl-3-(1-triazolyl)-3-deoxy-glycerol;

1-O-eicosyl-2-O-benzoyl-3-(1-pyrrolyl)-3-deoxy-glycerol;

S-1-O-octadecyl-2-O-benzoyl-3-(1-benztriazolyl)-3-deoxy-glycerol;

R-1-O-hexadecyl-2-O-benzoyl-3-(1-indolyl)-3-deoxy-glycerol;

1-O-(9-octadecenyl)-2-O-benzoyl-3-(1-pyrazolyl)-3-deoxy-glycerol; and

1-O-(8-hexadecenyl)-2-O-benzoyl-3-(1-triazolyl)-3-deoxy-glycerol.

Example 17
1-O-Octadecyl-3-(1-triazolyl)-3-deoxy-glycerol 5.0 Grams (10 mmol) of 1-O-octadecyl-2-O-benzoyl-3-(1-triazolyl)-3-deoxy-glycerol is dissolved in 100 mL ethanol, and 5 mL of 4N sodium hydroxide (20 mmol) in water is added at one time and allowed to stand overnight at room temperature. The ethanol is then removed under reduced pressure. 50 mL of 0.2N acetic acid in water and 150 mL toluene are then added. The phases are separated, and the toluene phase is washed two times with 50 mL water, dried over sodium sulfate and brought to dryness. The semisolid residue (3.82 g, 96.56% theoretical) of 1-O-octadecyl-3-(1-triazolyl)-3-deoxy-glycerol shows one spot in TLC; $R_f$=0.39, silica gel, methylene chloride/methanol 45/5, and is utilized in the succeeding step without further purification.

Example 18

Saponification of each of the Formula (K) compounds of Example 16 in accordance with the teaching of Example 17 yields the following respective compounds of Formula (N):

1-O-tetradecyl-3-(1-imidazolyl)-3-deoxy-glycerol;

1-O-hexadecyl-3-(1-triazolyl)-3-deoxy-glycerol;

1-O-eicosyl-3-(1-pyrrolyl)-3-deoxy-glycerol;

S-1-O-octadecyl-3-(1-benztriazolyl)-3-deoxy-glycerol;

R-1-O-hexadecyl-3-(1-indolyl)-3-deoxy-glycerol;

1-O-(9-octadecenyl)-3-(1-pyrazolyl)-3-deoxy-glycerol; and

1-O-(8-hexadecenyl)-3-(1-triazolyl)-3-deoxy-glycerol.

Example 19
rac-1-O-n-Octadecyl-3-(1-imidazolyl)-3-deoxy-glycerol, CPR 1150

A mixture of rac-1,2-epoxy-3-octadecyloxypropane (3.26 g, 10.0 mmol), imidazole (0.680 g, 10 mmol), anhydrous $K_2CO_3$ (40 mg), and 1,4-dioxane (20 mL) is stirred at 70–75° C. for 12 hours under a nitrogen atmosphere. The reaction mixture is concentrated in vacuo and dried in vacuo (0.5 mm Hg). A TLC of the resultant material indicated ($CHCl_3$/MeOH, 9/1, v/v) two spots at $R_f$=0.60 (product) and 0.2 (minor), respectively. Purification of the crude product by flash column chromatography (10×10 cm, silica gel 60, 230–400 mesh, eluent-$CHCl_3$/MeOH, 90/10, v/v) affords 1.8 g (yield 46%) pure rac-1-O-n-octadecyl-3-(1-imidazolyl)-deoxy-glycerol. TLC (thin-layer chromatography) (4×8 cm silica gel (0.25 mm thickness) plate, and $CHCl_3$/MeOH, 9/1, v/v) as eluent) give a single spot, $R_f$ value=0.60; m.p. 64–65° C.; FAB/Liquid Secondary Ion Mass Spectrometry (LSIMS) positive ion mode, 3-nitrobenzylalcohol matrix): (M+H)+at m/e 395.3; $^1H$ NMR ($CDCl^3$): 0.88 (t, 3 H, J=7Hz), 1.26 (br.s., 30 H), 1.58 (m, 2 H), 2.43 (br., 1 H), 3.33–3.47 (m, 4 H), 3.98–4.10 (m, 1 H), 4.04–4.10 (m, 3 H), 6.95 (s, 1 H), 7.01 (s, 1 H), 7.46 (s, 1 H); $^{13}C$ NMR ($CDCl_3$): 14.1, 22.1, 26.2, 29.0, 29.4, 29.5, 29.7, 31.9, 32.7, 50.3, 69.4, 71.6, 71.8, 119.9, 128.7, 137.7.

Example 20

Conversion of each of the Formula (M) compounds in accordance with the teaching of Example 19 yields the following respective compounds of Formula (N):

1-O-tetradecyl-3-(1-imidazolyl)-3-deoxy-glycerol;

1-O-hexadecyl-3-(1-triazolyl)-3-deoxy-glycerol;

1-O-eicosyl-3-(1-pyrrolyl)-3-deoxy-glycerol;

S-1-O-octadecyl-3-(1-benztriazolyl)-3-deoxy-glycerol;

R-1-O-hexadecyl-3-(1-indolyl)-3-deoxy-glycerol;

1-O-(9-octadecenyl)-3-(1-pyrazolyl)-3-deoxy-glycerol; and

1-O-(8-hexadecenyl)-3-(1-triazolyl)-3-deoxy-glycerol.

Example 21
1-O-Octadecyl-2-O-p-toluenesulfonyl-3-(1-imidazolyl)-3-deoxy-glycerol A mixture of 1-O-octadecyl-3-(1-imidazolyl)-3-deoxy-glycerol (10.0 g, 0.025 mol) and p-toluenesulfonyl chloride (47.7 g, 0.25 mol) in anhydrous 1:1 $CH_2Cl_2$-pyridine is stirred at 25° C. under nitrogen for 24 hours. The resultant mixture is filtered, concentrated in vacuo and recrystallized three times from ethanol-acetone to provide product.

Example 22

By following the procedure of Example 21, except that an equivalent amount of each of the appropriate Formula (N) compounds of Example 20 are utilized as the initial reactant, the following respective final products of Formula (O) are obtained.

1-O-tetradecyl-2-O-p-toluenesulfonate-3-(1-imidazolyl)-3-deoxy-glycerol;

1-O-hexadecyl-2-O-p-toluenesulfonate-3-(1-triazolyl)-3-deoxy-glycerol;

1-O-eicosyl-2-O-p-toluenesulfonate-3-(1-pyrrolyl)-3-deoxy-glycerol;

S-1-O-octadecyl-2-O-p-toluenesulfonate-3-(1-benztriazolyl)-3-deoxy-glycerol;

R-1-O-hexadecyl-2-O-p-toluenesulfonate-3-(1-indolyl)-3-deoxy-glycerol;

1-O-(9-octadecenyl)-2-O-p-toluenesulfonate-3-(1-pyrazolyl)-3-deoxy-glycerol; and 1-O-(8-hexadecenyl)-2-O-p-toluenesulfonate-3-(1-triazolyl)-3-deoxy-glycerol.

Example 23
1-O-Octadecyl-2-ethoxythiocarbonylthio-2-deoxy-3-(1-imidazolyl)-3-deoxy-glycerol A mixture of 1-O-octadecyl-2-O-p-toluenesulfonyl-3-(1-imidazolyl)-3-deoxy-glycerol (8.0 g, 0.0146 mol) and potassium O-ethylxanthate (7.02 g, 0.0438 mol) in deionized, degassed water 85 mL) is stirred at 25° C. for 24 h under a nitrogen atmosphere. The resultant mixture is concentrated in vacuo and then extracted with 1:1 $CH_2Cl_2$-ethyl acetate (500 mL). The organic extracts are dried over $MgSO_4$, gravity filtered and concentrated in vacuo to a 45 mL volume. The resultant solution is added to cold ether 300 mL to provide the product as a white powder.

Example 24

By following the procedure of Example 23, except that an equivalent amount of each of the appropriate Formula (O) compound of Example 22 are utilized as the initial reactant, the following respective final products of Formula (P) are obtained.

1-O-tetradecyl-2-ethoxythiocarbonylthio-2-deoxy-3-(1-imidazolyl)-3-deoxy-glycerol;

1-O-hexadecyl-2-ethoxythiocarbonylthio-2-deoxy-3-(1-triazolyl)-3-deoxy-glycerol;

1-O-eicosyl-2-ethoxythiocarbonylthio-2-deoxy-3-(1-pyrrolyl)-3-deoxy-glycerol;

S-1-O-octadecyl-2-ethoxythiopcarbonylthio-3-(1-benztriazolyl)-3-deoxy-glycerol;

R-1-O-hexadecyl-2-ethoxythiocarbonylthio-2-deoxy-3-(1-indolyl)-3-deoxy-glycerol;

1-O-(9-octadecenyl)-2-ethoxythiocarbonylthio-2-deoxy-3-(1-pyrazolyl)-3-deoxy-glycerol; and 1-O-(8-hexadecenyl)-2-ethoxythiocarbonylthio-2-deoxy-3-(1-triazolyl)-3-deoxy-glycerol.

Example 25
1-O-Octadecyl-2-thiol-2-deoxy-3-(1-imidazolyl)-3-deoxy-glycerol

A mixture of 1-O-octadecyl-2-ethoxythiocarbonylthio-2-deoxy- 3-(1-imidazolyl)-3-deoxy-glycerol (5.0 g, 0.0106 mol) and glycine (2.39, 0.0318 mol) in deionized, degassed water (21 mL) is stirred at 25° C. for 30 min. during which the reaction mixture is maintained at pH 9.5 by periodic addition of 2N aqueous NaOH (10.6 mL total added). The reaction mixture is then brought to pH 3 by addition of 6N aqueous HCl (5.5 mL) and then concentrated in vacuo. The resultant residue is dissolved into methylene chloride (85 mL), and the resultant methylene chloride solution is slowly poured into cold ether. The product which precipitates is collected by filtration, washed with ether and dried in vacuo to provide 1-O-octadecyl-2-thiol-2-deoxy-3-(i-imidazolyl)-3-deoxy-glycerol.

Example 26

By following the procedure of Example 25, except that an equivalent amount of each of the appropriate Formula (P) compounds of Example 24 are utilized as the initial reactant, the following respective final products of Formula (Q) are obtained.

1-O-tetradecyl-2-thiol-2-deoxy-3-(1-imidazolyl)-3-deoxy-glycerol;

1-O-hexadecyl-2-thiol-2-deoxy-3-(1-triazolyl)-3-deoxy-glycerol;

1-O-eicosyl-2-thiol-2-deoxy-3-(1-pyrrolyl)-3-deoxy-glycerol;

S-1-O-octadecyl-2-thiol-2-deoxy-3-(1-benztriazolyl)-3-deoxy-glycerol;

R-1-O-hexadecyl-2-thiol-2-deoxy-3-(1-indolyl)-3-deoxy-glycerol;

1-O-(9-octadecenyl)-2-thiol-2-deoxy-3-(1-pyrazolyl)-3-deoxy-glycerol; and

1-O-(8-hexadecenyl)-2-thiol-2-deoxy-3-(1-triazolyl)-3-deoxy-glycerol.

Example 27
2-O-Octadecyl-3-O-trityl-glycerol

A mixture of 2-O-octadecylglycerol (20 g, 58.8 mmol), obtained from conventional acid-catalyzed hydrolysis (HCl/MeOH) of 2-O-octadecyl-1,3-benzylideneglycerol, and triphenylmethylchloride (19.6, 70.56 mmol) in anhydrous pyridine (240 mL) is stirred for 48 h at room temperature under anhydrous conditions. The solution is poured into ice-cold water (500 mL), and the mixture is extracted with 3 portions (200 mL each) of light petroleum. The organic phase is washed with water (3×100 mL) and dried over anhydrous sodium sulfate. The solvent is evaporated, and light petroleum (180 mL) is added to the residue. On standing overnight some triphenylmethanol precipitates. The solid is filtered off, and the filtrate is evaporated to dryness. The crude product, which contains traces of unreacted 2-O-octadecylglycerol and some 1,3-di-O-trityl-2-O-octadecylglycerol, is purified by column chromatography on silica gel using a petroleum ether-diethyl ether gradient. The yield of pure 2-O-octadecyl-3-O-trityl-glycerol is 20.5 g (60%).

Example 28

The procedure of Example 27 is followed using an equivalent amount of the appropriate Formula (S) compound as the initial reactant to yield the following respective compounds of Formula (T):

2-O-tetradecyl-3-O-trityl-glycerol;

2-O-hexadecyl-3-O-trityl-glycerol;

2-O-eicosyl-3-O-trityl-glycerol; and

2-O-(9-octadecenyl)-3-O-trityl-glycerol.

Example 29
1-O-p-Toluenesulfonyl-2-O-octadecyl-3-O-trityl-glycerol

A solution of 2-O-octadecyl-3-O-trityl-glycerol (10 g, 17.04 mmol) in 52 mL anhydrous pyridine is added dropwise during 30 min. to a solution of p-toluenesulfonyl chloride (5.1 g, 26.75 mmol) in 39 mL anhydrous pyridine with stirring. After 2 days at room temperature, diethyl ether (162 mL) is added, and the precipitate formed is removed by filtration. The organic phase is washed successively with water (6×50 mL), 0.5N HCl (2×29 mL), 0.5N sodium carbonate (2×29 mL), and water (4×50 mL). Evaporation of the solvent in vacuo gives an oily product which becomes solid after drying in vacuo. The product, 1-O-p-toluenesulfonyl-2-O-octadecyl-3-O-trityl-glycerol (10.5 g, 85% yield), is used for the next step without purification.

Example 30

The procedure of Example 29 is followed using an equivalent amount of the appropriate Formula (T) compound as the initial reactant to yield the following respective compounds of Formula (U):

1-O-p-Toluenesulfonyl-2-O-tetradecyl-3-O-trityl-glycerol;

1-O-p-Toluenesulfonyl-2-O-hexadecyl-3-O-trityl-glycerol;

1-O-p-Toluenesulfonyl-2-O-eicosyl-3-O-trityl-glycerol; and

1-O-p-Toluenesulfonyl-2-O-(9-octadecenyl)-3-O-trityl-glycerol.

Example 31

1-(1-Imidazolyl)-1-deoxy-2-O-octadecyl-3-O-trityl-glycerol

The product of Example 29 (10.5 g, 14.1 mmol) and imidazole (2.88 g, 42.3 mmol) are dissolved in anhydrous dimethyl sulfoxide (80 mL) at 50° C. A solution of sodium dimethylsulfinylmethide, prepared from metallic sodium (0.648 g, 28.2 mg atoms) in dimethyl sulfoxide (80 mL), is added dropwise (over a 30 min. period) at 50° C. The reaction mixture is stirred at 100° C. (silicon oil bath) for 72 h. After cooling to room temperature, diethyl ether (210 mL) is added, and extraction with diethyl ether is repeated with 2×80 mL portions. The ether extracts are combined and washed with water (6×100 mL). The solution is dried over sodium sulfate, and the solvent is removed in vacuo. After drying the product in high vacuum, 8.1 g (90% yield) of crude 1-(1-imidazolyl)-1-deoxy-2-O-octadecyl-3-O-trityl-glycerol are obtained and used in the next step without purification.

Example 32

The procedure of Example 31 is followed using an equivalent amount of the appropriate Formula (U) compound as the initial reactant to yield the following respective compounds of Formula (V):

1-(1-triazolyl)-1-deoxy-2-O-octadecyl-3-O-trityl-glycerol;

1-(1-imidazolyl)-1-deoxy-2-O-hexadecyl-3-O-trityl-glycerol;

1-(1-pyrrolyl)-1-deoxy-2-O-tetradecyl-3-O-trityl-glycerol;

1-(1-benztriazolyl)-1-deoxy-2-O-eicosyl-3-O-trityl-glycerol; and 1-(1-indolyl)-1-deoxy-2-O-(9-octadecenyl)-3-O-trityl-glycerol.

Example 33

1-(1-Imidazolyl)-1-deoxy-2-O-octadecyl-glycerol

To the product of Example 31 (8.1 g, 12.86 mmol) in dichloromethane (200 mL) is added boron trifluoride (8 mL, 50% BF3 in methanol). The dark green solution is stirred at room temperature for 24 h. Then, 4N NaOH (approximately 22 mL) is added to bring the pH to 9.0. The organic phase is washed with water (5×100 mL) and dried over sodium sulfate. Evaporation of the solvent in vacuo gives 8.5 g of crude product which is purified by repeated column chromatography on silica gel. First run: column 28×2.8 cm; sequence of solvents:

1. chloroform (100 mL);
2. chloroform-methanol-35% ammonia (100: 0.5: 0.25; 201.5 mL)
3. chloroform-methanol-35% ammonia (100: 4: 0.25; 104.25 mL); and
4. chloroform-methanol-35% ammonia (100: 8: 0.25; 433 mL).

Flow rate: 12 mL/min., 15 mL fractions are collected and monitored by TLC, using chloroform-methanol (9:1) as the developing solvent. Fractions 22–29 (solvent 4) are combined, and the solvents evaporated to yield 3.5 g of product which is chromatographed on a 20×2 cm column, using the same sequence of solvents as for the first chromatography. Fractions 4–29 (solvent 4) are combined, and the solvents evaporated to give 2.46 g of 1-(1-imidazolyl)-1-deoxy-2-O-octadecyl-glycerol (50% yield) as a white solid.

Example 34

The procedure of Example 33 is followed using an equivalent amount of the appropriate Formula (V) compound as the initial reactant to yield the following respective compounds of Formula (W):

1-(1-triazolyl)-1-deoxy-2-O-octadecyl-glycerol;

1-(1-imidazolyl)-1-deoxy-2-O-hexadecyl-glycerol;

1-(1-pyrrolyl)-1-deoxy-2-O-tetradecyl-glycerol;

1-(1-benztriazolyl)-1-deoxy-2-O-eicosyl-glycerol; and 1-(1-indolyl)-1-deoxy-2-O-(9-octadecenyl)- glycerol.

Example 35

1-Bromo-1-deoxy-2-O-octadecyl-3-benzoyl-glycerol 8.65 Grams (20 mmol) of 2-O-octadecyl-1,3-benzylidene-glycerol is reacted with 3.92 g (22 mmol) of N-bromosuccinimide and 8.90 g (40 mmol) of barium carbonate in 100 mL carbon tetrachloride at reflux with stirring for two hours. The reaction mixture is filtered, and the filter cake is washed twice with carbon tetrachloride and evaporated to dryness. The residue is taken up in 40 mL of toluene and purified by column chromatography on silica gel with toluene/cyclohexane (3/2) as the mobile phase. Removal of the solvent yields 6.83 g (66.70% theoretical) of pure 1-bromo-1-deoxy-2-O-octadecyl-3-O-benzoyl-glycerol; $R_f$=0.21, silica gel, toluene.

Example 36

The procedure of Example 35 is followed using an equivalent amount of the appropriate Formula (R) compound as the initial reactant to yield the following respective compounds of Formula (X):

1-bromo-1-deoxy-2-O-tetradecyl-3-O-benzoyl-glycerol;

1-bromo-1-deoxy-2-O-hexadecyl-3-O-benzoyl-glycerol;

1-bromo-1-deoxy-2-O-eicosyl-3-O-benzoyl-glycerol; and 1-bromo-1-deoxy-2-O-(9-octadecenyl)-3-O-benzoyl-glycerol.

Example 37

1-(1-(2-Methyl)-imidazolyl)-1-deoxy-2-O-octadecyl-3-O-benzoyl-glycerol

Ten millimoles of 1-bromo-1-deoxy-2-O-octadecyl-3-O-benzoyl-glycerol is reacted with the Het-Compound, 2-methylimidazole, in accordance with the procedure outlined in Example 3 (step 2 of Reaction Scheme 1) utilizing the same conditions and molar ratios. After completion of the reaction, workup and purification as therein described, about 2.89 g (56.3% theoretical) of the Formula (T) compound, 1-(1-(2-methyl)-imidazolyl)-1-deoxy-2-O-octadecyl-3-benzoyl-glycerol, is obtained; Rf=0.58, silica gel, $CH_2Cl_2$/$CH_3OH$ 45/5.

Example 38

By following the procedure of Example 37, except that an equivalent amount of each of the Formula (X) compounds of Example 36 and the appropriate Het-Compounds are the reactants, the following respective compounds of Formula (Y) are obtained:

- 1-(1-triazolyl)-1-deoxy-2-O-octadecyl-3-O-benzoyl-glycerol;
- 1-(1-imidazolyl)-1-deoxy-2-O-hexadecyl-3-O-benzoyl-glycerol;
- 1-(1-pyrrolyl)-1-deoxy-2-O-tetradecyl-3-O-benzoyl-glycerol;
- 1-(1-benztriazolyl)-1-deoxy-2-O-eicosyl-3-O-benzoyl-glycerol; and
- 1-(1-indolyl)-1-deoxy-2-O-(9-octadecenyl)-3-O-benzoyl-glycerol.

Example 39

1-(1-(2-Methyl)-imidazolyl)-1-deoxy-2-O-octadecyl-glycerol

Ten millimole of 1-(1-(2-methyl)-imidazolyl)-1-deoxy-2-O-octadecyl-3-O-benzoyl chloride is debenzoylated in accordance with the procedure outlined in Example 13 (step 3 of Reaction Scheme 3) utilizing the same conditions and molar ratios to yield about 4.0 1 g of the Formula (R) compound, 1-(1-(2-methyl)-imidazolyl)-1-deoxy-2-O-octadecyl-glycerol; $R_f$=0.37, silica gel, $CH_2Cl_2/CH_3OH$ 45/5.

Example 40

Debenzoylation of each Formula (Y) compound of Example 38 in accordance with the procedure of Example 17 affords the following respective compounds of Formula (W):

- 1-(1-triazolyl)-1-deoxy-2-O-octadecyl-glycerol;
- 1-(1-imidazolyl)-1-deoxy-2-O-hexadecyl-glycerol;
- 1-(1-pyrrolyl)-1-deoxy-2-O-tetradecyl-glycerol;
- 1-(1-benztriazolyl)-1-deoxy-2-O-eicosyl-glycerol; and
- 1-(1-indolyl)-1-deoxy-2-O-(9-octadecenyl)-glycerol.

Example 41

1-(1-Imidazolyl)-1-deoxy-2-O-octadecyl-3-O-p-toluenesulfonyl-glycerol

A mixture of 1-(1-imidazolyl)-1-deoxy-2-O-octadecyl-glycerol (10.0 g, 0.025 mol) and p-toluenesulfonyl chloride (47.7 g, 0.25 mol) in anhydrous 1:1 $CH_2Cl_2$-pyridine is stirred at 25° C. under nitrogen for 24 hours. The resultant mixture is filtered, concentrated in vacuo and recrystallized three times from ethanol-acetone to provide product.

Example 42

By following the procedure of Example 41, except that an equivalent amount each of the appropriate Formula (W) compounds of Example 40 are utilized as the initial reactant, the following respective final products of Formula (Z) are obtained.

- 1-(1-triazolyl)-1-deoxy-2-O-octadecyl-3-O-p-toluenesulfonate-glycerol;
- 1-(1-imidazolyl)-1-deoxy-2-O-hexadecyl-3-O-p-toluenesulfonate-glycerol;
- 1-(1-pyrrolyl)-1-deoxy-2-O-tetradecyl-3-O-p-toluenesulfonate-glycerol;
- 1-(1-benztriazolyl)-1-deoxy-2-O-eicosyl-3-O-p-toluenesulfonate-glycerol; and
- 1-(1-indolyl)-1-deoxy-2-O-(9-octadecenyl)-3-O-p-toluenesulfonate-glycerol.

Example 43

1-(1-Imidazolyl)-1-deoxy-2-O-octadecyl-3-ethoxythiocarbonylthio-3-deoxy-glycerol A mixture of 1-(1-imidazolyl)-1-deoxy-2-O-octadecyl-O-p-toluenesulfonyl-glycerol (8.0 g, 0.0146 mol) and potassium O-ethylxanthate (7.02 g, 0.0438 mol) in deionized, degassed water 85 mL) is stirred at 25° C. for 24 h under a nitrogen atmosphere. The resultant mixture is concentrated in vacuo and then extracted with 1:1 $CH_2Cl_2$-ethyl acetate (500 mL). The organic extracts are dried over $MgSO_4$, gravity filtered and concentrated in vacuo to a 45 mL volume. The resultant solution is added to cold ether 300 mL to provide 1-(1-imidazolyl)-1-deoxy-2-O-octadecyl-3-ethoxythiocarbonylthio-3-deoxy-glycerol as a white powder.

Example 44

By following the procedure of Example 43, except that an equivalent amount of each of the appropriate Formula (Z) compounds of Example 42 is utilized as the initial reactant, the following respective final products of Formula (AA) are obtained.

- 1-(1-triazolyl)-1-deoxy-2-O-octadecyl-3-ethoxythiocarbonylthio-3-deoxy-glycerol;
- 1-(1-imidazolyl)-1-deoxy-2-O-hexadecyl-3-ethoxythiocarbonylthio-3-deoxy-glycerol;
- 1-(1-pyrrolyl)-1-deoxy-2-O-tetradecyl-3-ethoxythiocarbonylthio-3-deoxy-glycerol;
- 1-(1-benztriazolyl)-1-deoxy-2-O-eicosyl-3-ethoxythiocarbonylthio-3-deoxy-glycerol; and
- 1-(1-indolyl)-1-deoxy-2-O-(9-octadecenyl)-3-ethoxythiocarbonylthio-3-deoxy-glycerol.

Example 45

1-(1-Imidazolyl)-1-deoxy-2-O-octadecyl-3-thiol-3-deoxy-glycerol

A mixture of 1-(1-imidazolyl)-1-deoxy-2-O-octadecyl-3-ethoxythiocarbonylthio-3-deoxy-glycerol (5.0 g, 0.0106 mol) and glycine (2.39, 0.0318 mol) in deionized, degassed water (21 mL) is stirred at 25° C. for 30 min. during which the reaction mixture is maintained at pH 9.5 by periodic addition of 2N aqueous NaOH (10.6 mL total added). The reaction mixture is then brought to pH 3 by addition of 6N aqueous HCl (5.5 mL) and then concentrated in vacuo. The resultant residue is dissolved into methylene chloride (85 mL), and the resultant methylene chloride solution is slowly poured into cold ether. The product which precipitates is collected by filtration, washed with ether and dried in vacuo to provide 1-(1-imidazolyl)-1-deoxy-2-O-octadecyl-3-thiol-3-deoxy-glycero.

Example 46

By following the procedure of Example 45, except that an equivalent amount of each of the appropriate Formula (AA) compounds of Example 44 is utilized as the initial reactant, the following respective final products of Formula (BB) are obtained.

- 1-(1-triazolyl)-1-deoxy-2-O-octadecyl-3-thiol-3-deoxy-glycerol;
- 1-(1-imidazolyl)-1-deoxy-2-O-hexadecyl-3-thiol-3-deoxy-glycerol;
- 1-(1-pyrrolyl)-1-deoxy-2-O-tetradecyl-3-thiol-3-deoxy-glycerol;

1-(1-benztriazolyl)-1-deoxy-2-O-eicosyl-3-thiol-3-deoxy-glycerol; and 1-(1-indolyl)-1-deoxy-2-O-(9-octadecenyl)-3-thiol-3-deoxy-glycerol.

Example 47

A. Injection—For 1000 Ampules:

| Ingredient | Amount |
|---|---|
| Formula I Compound or Salt | 5 g |
| Buffering Agents | q.s. |
| Propylene Glycol | 400 mg |
| Water for Injection | 600 mL |

The active compound and buffering agents are dissolved in the propylene glycol at about 50° C. The water for injection is then added with stirring and the resulting solution is filtered, filled into ampules, sealed and sterilized by autoclaving.

B. Capsule—For 1000 Capsules:

| Ingredient | Amount |
|---|---|
| Formula I Compound or Salt | 50 g |
| Lactose | 450 g |
| Magnesium Stearate | 5 g |

The ingredients are thoroughly mixed and packed into gelatin capsules.

C. Ointment

| Ingredient | Amount |
|---|---|
| Formula I Compound or Salt | 0.1 to 5.0% |
| Ointment Base | q.s. |

A conventional ointment base containing mineral oil and white petrolatum is prepared using relative proportions of each to achieve the desired viscosity. The active compound is added and thoroughly blended to form a homogeneous ointment. For treating viral infections, an effective amount of a topical corticosteroid, such as 0.05% betamethasone dipropionate or 0.1% triamcinolone acetonide, may also be blended into the ointment.

D. Tablets—For 1000 Tablets:

| Ingredient | Amount |
|---|---|
| Formula I Compound or Salt | 50 g |
| Starch | 20 g |
| Magnesium Stearate | 1 g |

The active compound and the starch are granulated with water and dried. The magnesium stearate is added to the dried granules and the mixture is thoroughly blended and molded into tablets.

What is claimed is:

1. Heteroaryl-substituted glycerols of Formulas Ia, Ib, and Ic:

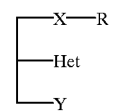

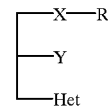

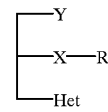

wherein X is oxygen or sulfur;

R is a substituted or unsubstituted straight or branched chain $C_{14}$–$C_{30}$ alkyl or $C_{14}$–$C_{30}$ alkenyl, provided that a double bond of the alkenyl does not originate at a carbon atom bonded to X, and the substituents on R being one or more of halo, $C_1$–$C_3$ alkoxy, or cyano;

Het represents a 5- to 9-membered heteroaryl mono- or bicyclic ring system having no more than 1 carbonyl carbon in the ring system, with 1 to 4 nitrogen atoms as the sole heteroatoms, one of which nitrogens is bonded to the glycero carbon;

Y is hydroxyl or thiol; and enantiomeric and cis and trans geometric isomers thereof, and pharmaceutically-acceptable salts thereof.

2. A compound of claim 1 wherein Het is itidazolyl or triazolyl.

3. A compound of claim 1 having a structure as depicted in Formula Ia.

4. A compound of claim 1 wherein R is $C_{14\text{-}20}$ alkyl or $C_{14\text{-}20}$ alkenyl.

5. A compound of claim 1 wherein R is $C_{16\text{-}18}$ alkyl or $C_{16\text{-}18}$ alkenyl.

6. A compound of claim 1 having a structure as depicted in Formula Ia and further wherein Het is imidazolyl or triazolyl and R is $C_{16\text{-}18}$ alkyl.

7. The compound of claim 1 which is selected from the group consisting of:

1-O-octadecyl-2-(1-imidazolyl)-2-deoxy-glycerol;

1-O-octadecyl-2-(1-triazolyl)-2-deoxy-glycerol; and

1-O-hexadecyl-2-(1-imidazolyl)-2-deoxy-glycerol.

8. The compound of claim 1 which is 1-O-octadecyl-3-(1-imidazolyl)-3-deoxy-glycerol.

9. A method of treating viral infection in mammals comprising administering to a mammal an antiviral-effective amount of one or more compounds of claim 1 or a pharmaceutically-acceptable salt thereof.

10. The method of claim 9 wherein a compound where Het is imidazolyl or triazolyl is administered.

11. The method of claim 9 wherein a compound having a structure as depicted in Formula Ia is administered.

12. The method of claim 9 wherein a compound where R is $C_{14\text{-}20}$ alkyl or $C_{14\text{-}20}$ alkenyl is administered.

13. The method of claim 9 wherein a compound where R is $C_{16\text{-}18}$ alkyl or $C_{16\text{-}18}$ alkenyl is administered.

14. The method of claim 9 wherein a compound having a structure as depicted in Formula Ia and further wherein Het is imidazolyl or triazolyl and R is $C_{16\text{-}18}$ alkyl is administered.

15. The method of claim 9 wherein a compound selected from the group consisting of 1-O-octadecyl-2-(1-imidazolyl)-2-deoxy-glycerol;

1-O-octadecyl-2-(1-triazolyl)-2-deoxy-glycerol; and

1-O-hexadecyl-2-(1-imidazolyl)-2-deoxy-glycerol is administered.

16. The method of claim 9 wherein 1-O-octadecyl-3-(1-imidazolyl)-3-deoxy-glycerol is administered.

17. A method of treating bacterial infection in mammals comprising administering to a mammal an antibacterial-effective amount of one or more compounds of claim 1 or a pharmaceutically-acceptable salt thereof.

18. The method of claim 17 wherein a compound where Het is imidazolyl or triazolyl is administered.

19. The method of claim 17 wherein a compound having a structure as depicted in Formula Ia is administered.

20. The method of claim 17 wherein a compound where R is $C_{14-20}$ alkyl or $C_{14-20}$ alkenyl is administered.

21. The method of claim 17 wherein a compound where R is $C_{16-18}$ alkyl or $C_{16-18}$ alkenyl is administered.

22. The method of claim 17 wherein a compound having a structure as depicted in Formula Ia and further wherein Het is imidazolyl or triazolyl and R is $C_{16-18}$ alkyl is administered.

23. The method of claim 17 wherein a compound selected from the group consisting of 1-O-octadecyl-2-(1-imidazolyl)-2-deoxy-glycerol;

1-O-octadecyl-2-(1-triazolyl)-2-deoxy-glycerol; and

1-O-hexadecyl-2-(1-imidazolyl)-2-deoxy-glycerol is administered.

24. The method of claim 17 wherein 1-O-octadecyl-3-(1-imidazolyl)-3-deoxy-glycerol is administered.

25. A pharmaceutical composition comprising an antiviral- or antibacterial-effective amount of a compound of claim 1 or a pharmaceutically-acceptable salt thereof in combination with a pharmaceutically-acceptable liquid or solid carrier.

26. The composition of claim 25 comprising a compound wherein Het is imidazolyl or triazolyl.

27. The composition of claim 25 comprising a compound having a structure as depicted in Formula Ia.

28. The composition of claim 25 comprising a compound wherein R is $C_{14-20}$ alkyl or $C_{14-20}$ alkenyl.

29. The composition of claim 25 comprising a compound wherein R is $C_{16-18}$ all or $C_{16-18}$ alkenyl.

30. The composition of claim 25 comprising a compound having a structure as depicted in Formula Ia and further in which Het is imidazolyl or triazolyl and R is $C_{16-18}$ alkyl.

31. The composition of claim 25 comprising one or more compounds selected from the group consisting of 1-O-octadecyl-2-(1-imidazolyl)-2-deoxy-glycerol;

1-O-octadecyl-2-(1-triazolyl)-2-deoxy-glycerol; and

1-O-hexadecyl-2-(1-imidazolyl)-2-deoxy-glycerol.

32. The composition of claim 25 comprising 1-O-octadecyl-3-(1-imidazolyl)-3-deoxy-glycerol.

33. A pharmaceutical composition for topical use comprising from about 0.1 to about 5.0 weight percent of a compound of claim 1 and a pharmaceutically-acceptable topical carrier.

* * * * *

UNITED STATES PATENT AND TRADEMARK OFFICE
CERTIFICATE OF CORRECTION

PATENT NO. : 5,972,982
DATED : October 26, 1999
INVENTOR(S) : NAIR et al.

It is certified that error appears in the above-identified patent and that said Letters Patent is hereby corrected as shown below:

In claim 2, column 32, line 34, delete "itidazolyl" and insert therefor -- imidazolyl --.

Signed and Sealed this

Twenty-fifth Day of April, 2000

Attest:

Q. TODD DICKINSON

Attesting Officer

Director of Patents and Trademarks